United States Patent [19]

Geach et al.

[11] Patent Number: 5,114,461

[45] Date of Patent: May 19, 1992

[54] CYCLIC DIONES

[75] Inventors: Neil J. Geach, Brentwood; James Gilmour, Barkingside; Leslie R. Hatton, Chelmsford; Philip H. G. Smith, Brentwood, all of England

[73] Assignee: May & Baker Limited, United Kingdom

[21] Appl. No.: 440,208

[22] Filed: Nov. 22, 1989

Related U.S. Application Data

[63] Continuation of Ser. No. 154,031, Feb. 9, 1988, abandoned.

[30] Foreign Application Priority Data

Feb. 11, 1987 [GB] United Kingdom ............... 8703068
Mar. 31, 1987 [GB] United Kingdom ............... 8707608

[51] Int. Cl.$^5$ .................... A01N 43/02; A01N 305/04; A01N 43/40

[52] U.S. Cl. .................................... 71/88; 71/90; 71/94; 71/98; 71/103; 71/118; 71/121; 71/123; 568/306; 568/329; 549/13; 549/14; 549/28; 549/274; 549/291; 549/265; 544/158; 544/159; 544/162; 544/170; 544/163; 546/220

[58] Field of Search .............. 546/220; 71/94, 88, 71/90, 98, 103, 118, 121, 123; 549/274, 291, 265, 28, 13, 14; 544/158, 159, 162, 163, 170; 568/306, 329

[56] References Cited

U.S. PATENT DOCUMENTS 4,808,720 2/1989 Curtis ........................ 71/94

Primary Examiner—C. Warren Ivy
Assistant Examiner—Amelia A. Owens
Attorney, Agent, or Firm—Burns, Doane, Swecker & Mathis

[57] ABSTRACT

A 2-benzoylcyclic-1,3-dione derivative of the formula:

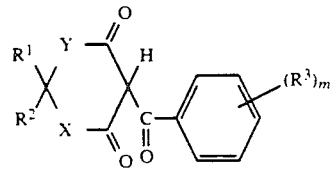

wherein X represents methylene, oxygen, sulphur or $-NR^4-$, Y represents $-C(R^5)(R^6)-$ or oxygen, $R^1$ represents hydrogen or alkyl optionally substituted by halogen or represents cycloalkyl, $R^2$ represents hydrogen or $R^7$ or $R^1$ and $R^2$ together represent alkylene, $R^3$ represents halogen, hydroxy, carboxy, nitro, cyano or amino or carbamoyl (which may be substituted by one or two alkyl groups), alkoxycarbonyl, alkanoyl, or alkanoylamino, R, RO, RS, RSO or $RSO_2$ in which R represents alkyl optionally substituted by halogen, $R^4$ represents hydrogen or alkyl or alkoxycarbonyl, $R^5$ represents hydrogen or alkyl or alkoxycarbonyl, $R^6$ represents hydrogen or alkyl, $R^7$ represents alkyl which may be substituted by halogen or alkylthio or by a group $(R^8)_n$-phenyl-S-, or represents cycloalkyl or tetrahydrothiapyran-3-yl or represents a group $(R^8)_n$-phenyl- in which $R^8$ represents a halogen, hydroxy, carboxy, nitro or cyano, or amino or carbamoyl (which may be substituted by one or two alkyl groups), alkoxycarbonyl or alkanoyl or alkanoylamino or R, RO, RS, RSO or $RSO_2$ in which R represents alkyl which is optionally substituted by halogen, m is zero or 1 to 5 and n is zero or 1 to 5, provided that when X represents methylene, and Y represents $-C(R^5)(R^6)-$ then $R^1$ and $R^2$ do nmot simultaneously represent hydrogen or alkyl and salts thereof are useful as herbicides.

15 Claims, No Drawings

CYCLIC DIONES

This application is a continuation of application Ser. No. 07/154,031, filed Feb. 9, 1988 now abandoned.

This invention relates to 2-benzoylcyclic-1,3-dione derivatives, compositions containing them and their use as herbicides.

The present invention provides new 2-benzoylcyclic-1,3-dione derivatives of the general formula I herein depicted wherein X represents the methylene group, an oxygen or sulphur atom or a group —$NR^4$—, Y represents a methylene group —$C(R^5)(R^6)$— or the oxygen atom, $R^1$ represents the hydrogen atom or a straight- or branched-chain alkyl group containing from 1 to 6 carbon atoms which is optionally substituted by one or more halogen atoms or represents a cycloalkyl group containing from 3 to 6 carbon atoms, $R^2$ represents the hydrogen atom or a group $R^7$ or $R^1$ and $R^2$ together represent an alkylene group containing from 2 to 6 carbon atoms, $R^3$ represent a halogen atom, a hydroxy, carboxy, nitro or cyano group, an amino or carbamoyl group (which may be substituted by one or two straight- or branched-chain alkyl groups containing from 1 to 6 carbon atoms), a straight- or branched-chain alkoxycarbonyl or alkanoyl or alkanoylamino group containing from 2 to 7 carbon atoms or a group R, RO, RS, RSO or $RSO_2$ in which R represents a straight- or branched-chain alkyl group containing from 1 to 6 carbon atoms which is optionally substituted by one or more halogen atoms, $R^4$ represents the hydrogen atom or a straight- or branched-chain alkyl or alkoxycarbonyl group containing from 1 to 6 or from 2 to 7 carbon atoms respectively, $R^5$ represents the hydrogen atom or a straight- or branched-chain alkyl or alkoxycarbonyl group containing from 1 to 6 or from 2 to 7 carbon atoms respectively, $R^6$ represents the hydrogen atom or a straight- or branched-chain alkyl group containing from 1 to 6 carbon atoms, $R^7$ represents a straight- or branched-chain alkyl group containing from 1 to 6 carbon atoms which may be substituted by one or more halogen atoms or a straight- or branched-chain alkylthio group containing from 1 to 6 carbon atoms or by a group $(R^8)_n$-phenyl-S-, or represents a cycloalkyl group containing from 3 to 6 carbon atoms, e.g. the cyclohexyl group or the tetrahydrothiapyran-3-yl group or represents a group $(R^8)_n$-phenyl- in which $R^8$ represents a halogen atom, a hydroxy, carboxy, nitro or cyano group, an amino or carbamoyl group (which may be substituted by one or two straight- or branched-chain alkyl groups containing from 1 to 6 carbon atoms), a straight- or branched-chain alkoxycarbonyl or alkanoyl or alkanoylamino group containing from 2 to 7 carbon atoms or a group R, RO, RS, RSO or $RSO_2$ in which R represents a straight- or branched-chain alkyl group containing from 1 to 6 carbon atoms which is optionally substituted by one or more halogen atoms, m is zero or an integer from 1 to 5 and n is zero or an integer from 1 to 5, provided that when X represents the methylene group, and Y represents a methylene group —$C(R^5)(R^6)$— then $R^1$ and $R^2$ do not simultaneously represent a hydrogen atom or a straight- or branched-chain alkyl group containing from 1 to 6 carbon atoms, and agriculturally acceptable salts thereof, which possess valuable herbicidal properties.

It is to be understood that when m or n is an integer from 2 to 5, the substituents $R^3$ and $R^8$ respectively may be the same or different.

Furthermore, it will be understood by those skilled in the art that the compounds of formula I exhibit tautomerism such that the hydrogen atom at the benzoyl substituted-position of the ring may reside on any of the oxygen atoms substituted in the adjacent positions, and that the forms thus described may be present to a greater or lesser degree and are in a state of dynamic equilibrium with each other. The chiral carbon atoms at the other positions of the ring give rise to stereoisomers. Furthermore, in certain cases the substituents $R^1$, $R^2$, $R^3$, $R^4$, $R^5$, $R^6$, $R^7$ and $R^8$ contribute to optical and/or stereoisomerism. All such forms are embraced by the present invention.

The agriculturally acceptable salts of the compounds of general formula I include salts with agriculturally acceptable bases and acids i.e. salts the cations or anions of which are known and accepted in the art for the formation of salts for agricultural or horticultural use. Preferably, the salts are water-soluble. Suitable salts with bases include alkali metal (e.g. sodium and potassium), alkaline earth metal (e.g. calcium and magnesium), ammonium and amine (e.g. diethanolamine, triethanolamine, octylamine, morpholine and dioctylmethylamine) salts. Suitable acid addition salts of the compounds of general formula I, which may be formed when the compounds incorporate an amino radical, include salts with inorganic acids, for example hydrochlorides, sulphates, phosphates and nitrates and salts with organic acids, for example acetic acid. It is to be understood that where reference is made in the present specification to the compounds of general formula I, such reference is intended to include also the salts with agriculturally acceptable bases or acids of compounds of general formula I, where appropriate.

Preferred compounds of formula I are those wherein X represent a group —$NR^4$—, Y represents a methylene group —$C(R^5)(R^6)$—, $R^2$ represents an alkyl or optionally substituted phenyl group as hereinbefore defined for $R^7$ and the other symbols are as hereinbefore defined.

Of particular interest as herbicides are the following classes of compounds of general formula I:

Compounds wherein Y represents a methylene group —$C(R^5)(R^6)$—;

Compounds wherein $R^2$ represents the hydrogen atom or a straight- or branched-chain alkyl group containing from 1 to 6 carbon atoms which is optionally substituted by one or more halogen atoms or a cycloalkyl group containing from 3 to 6 carbon atoms, or represents a group $(R^8)_n$-phenyl-, or $R^1$ and $R^2$ together represent an alkylene group containing from 2 to 6 carbon atoms;

Compounds wherein $R^1$ represents a straight- or branched-chain alkyl group containing from 1 to 6 carbon atoms which is substituted by one or more halogen atoms or a cycloalkyl group containing from 3 to 6 carbon atoms and $R^2$ represents a group $(R^8)_n$-phenyl-;

Compounds wherein X represents the methylene group, an oxygen or sulphur atom or a group —$NR^4$—, in which $R^4$ represents the hydrogen atom or a straight- or branched-chain alkyl group containing from 1 to 6 carbon atoms. Y represents a methylene group —$C(R^5)(R^6)$—, $R^1$ represents the hydrogen atom or a straight- or branched-chain alkyl group containing from 1 to 6 carbon atoms which is optionally substituted by one or more halogen atoms or a cycloalkyl group containing from 3 to 6 carbon atoms, $R^2$ represents a straight- or branched-chain alkyl group containing from 1 to 6 carbon atoms which is substituted by one or more halogen atoms or a cycloalkyl group containing from 3 to 6 carbon atoms or $R^1$ and $R^2$ together represent an alkylene group containing from 2 to 6 carbon atoms;

Compounds wherein X represents the group —NH—, Y represents a methylene group —C($R^5$)($R^6$)—, $R^1$ represents the hydrogen atom or a straight- or branched-chain alkyl group containing from 1 to 6 carbon atoms, $R^2$ represents the hydrogen atom or a straight- or branched-chain alkyl group containing from 1 to 6 carbon atoms;

Compounds wherein X represents the methylene group, Y represents a methylene group —C($R^5$)($R^6$)—, (preferably not the methylene group —CH$_2$—), $R^1$ represents the hydrogen atom or a straight- or branched-chain alkyl group containing from 1 to 6 carbon atoms and $R^2$ represents a group ($R^8$)$_n$-phenyl- and in which one of $R^3$ is preferably a hydroxy, carboxy, nitro or cyano group, an amino or carbamoyl group (which may be substituted by one or two straight- or branched-chain alkyl groups containing from 1 to 6 carbon atoms), a straight- or branched-chain alkyl or alkoxy group substituted by one or more halogen atoms, e.g. trifluoromethyl or trifluoromethoxy, or an alkoxycarbonyl or alkanoyl or alkanoylamino group containing from 1 to 6 or from 2 to 7 carbon atoms, respectively, or a group RS, RSO or RSO$_2$ in which R represents a straight- or branched-chain alkyl group containing from 1 to 6 carbon atoms which is optionally substituted by one or more halogen atoms and is more preferably the nitro group;

Compounds wherein X represents an oxygen or sulphur atom, Y represents a methylene group —C($R^5$)($R^6$)—, $R^1$ represents the hydrogen atom or a straight- or branched-chain alkyl group containing from 1 to 6 carbon atoms and $R^2$ represents a group ($R^8$)$_n$-phenyl-;

Compounds wherein ($R^3$)$_m$ substitution is 2-chloro, 2-trifluoromethyl or preferably 2-nitro, with 4-trifluoromethoxy, 4-trifluoromethylthio/sulphinyl/sulphonyl or preferably 4-chloro, 4-trifluoromethyl or 4-methylsulphonyl and preferably without substitution in the 6-position of the benzoyl group; 2-nitro and 4-chloro-2-nitro are especially preferred.

Of particular interest as herbicides are the following compounds of formula I:

1. 3-(4-chloro-2-nitrobenzoyl)-6,6-dimethylpiperidine-2,4-dione
2. 3-(2-nitrobenzoyl)-6-phenylpiperidine-2,4-dione
3. 3-(4-chloro-2-nitrobenzoyl)-6-phenylpiperidine-2,4-dione
4. 1-methyl-3-(2-nitrobenzoyl)-6-phenylpiperidine-2,4-dione
5. 6,6-dimethyl-3-(2-nitrobenzoyl)piperidine-2,4-dione
6. 3-(4-chloro-2-nitrobenzoyl)piperidine-2,4-dione
7. 3-(4-chloro-2-nitrobenzoyl)-5-methylpiperidine-2,4-dione
8. 3-(4-chloro-2-nitrobenzoyl)-1-methylpiperidine-2,4-dione
9. 3-(4-chloro-2-nitrobenzoyl)-6-methyl-6-phenylpiperidine-2,4-dione
10. 3-(4-chloro-2-nitrobenzoyl)-6-methylpiperidine-2,4-dione
11. 3-(3,4-dichlorobenzoyl)-6-phenylpiperidine-2,4-dione
12. 3-(3-bromobenzoyl)-6-phenylpiperidine-2,4-dione
13. 3-(2,6-dichlorobenzoyl)-6-phenylpiperidine-2,4-dione
14. 3-(5-methyl-2-nitrobenzoyl)-6-phenylpiperidine-2,4-dione
15. 3-(4-trifluoromethylbenzoyl)-6-phenylpiperidine-2,4-dione
16. 3-(4-fluorobenzoyl)-6-phenylpiperidine-2,4-dione
17. 3-(2-chlorobenzoyl)-6-phenylpiperidine-2,4-dione
18. 3-(2-trifluoromethylbenzoyl)-6-phenylpiperidine-2,4-dione
19. 3-(2-fluorobenzoyl)-6-phenylpiperidine-2,4-dione
20. 3-(2,4-bistrifluoromethylbenzoyl)-6-phenylpiperidine-2,4-dione
21. 3-(2-bromobenzoyl)-6-phenylpiperidine-2,4-dione
22. 3-(2-iodobenzoyl)-6-phenylpiperidine-2,4-dione
23. 3-(2-methylbenzoyl)-6-phenylpiperidine-2,4-dione
24. 3-benzoyl-6-phenylpiperidine-2,4-dione
25. 3-(2-chloro-4-fluorobenzoyl)-6-phenylpiperidine-2,4-dione
26. 3-(4-bromo-2-nitrobenzoyl)-6-phenylpiperidine-2,4-dione
27. 3-(2-nitro-4-trifluoromethylbenzoyl)-6-phenylpiperidine-2,4-dione
28. 3-(2-methoxybenzoyl)-6-phenylpiperidine-2,4-dione
29. 3-(4-acetyl-2-nitrobenzoyl)-6-phenylpiperidine-2,4-dione
30. 3-(2-methylthiobenzoyl)-6-phenylpiperidine-2,4-dione
31. 3-(2-trifluoromethoxybenzoyl)-6-phenylpiperidine-2,4-dione
32. 3-(2,3,4-trichlorobenzoyl)-6-phenylpiperidine-2,4-dione
33. 3-(2,4,5-trichlorobenzoyl)-6-phenylpiperidine-2,4-dione
34. 3-(4-methoxy-2-nitrobenzoyl)-6-phenylpiperidine-2,4-dione
35. 3-(5-chloro-2-nitrobenzoyl)-6-phenylpiperidine-2,4-dione
36. 3-(2-ethoxybenzoyl)-6-phenylpiperidine-2,4-dione
37. 3-(3-nitrobenzoyl)-6-phenylpiperidine-2,4-dione
38. 3-(3-chlorobenzoyl)-6-phenylpiperidine-2,4-dione
39. 3-(3-trifluoromethoxybenzoyl)-6-phenylpiperidine-2,4-dione
40. 3-(3-trifluoromethylbenzoyl)-6-phenylpiperidine-2,4-dione
41. 3-(3-methylbenzoyl)-6-phenylpiperidine-2,4-dione
42. 3-(3-methoxybenzoyl)-6-phenylpiperidine-2,4-dione
43. 3-(4-tert-butylbenzoyl)-6-phenylpiperidine-2,4-dione
44. 3-(4-iodobenzoyl)-6-phenylpiperidine-2,4-dione
45. 3-(4-chloro-2-nitrobenzoyl)-6-(3,4-difluorophenyl)-piperidine-2,4-dione
46. 3-(4-chloro-2-nitrobenzoyl)-6-(4-methylphenyl)-piperidine-2,4-dione
47. 3-(4-chloro-2-nitrobenzoyl)-6-(4-methoxyphenyl)-piperidine-2,4-dione
48. 3-(4-chloro-2-nitrobenzoyl)-6-(3-chlorophenyl)-piperidine-2,4-dione
49. 3-(4-chloro-2-nitrobenzoyl)-6-(4-methylthiophenyl)-piperidine-2,4-dione
50. 3-(4-chloro-2-nitrobenzoyl)-6-(4-methylsulphinylphenyl)-piperidine-2,4-dione
51. 3-(4-chloro-2-nitrobenzoyl)-6-(4-methylsulphonylphenyl)-piperidine-2,4-dione
52. 3-(4-chloro-2-nitrobenzoyl)-6-(2-bromophenyl)-piperidine-2,4-dione
53. 3-(4-chloro-2-nitrobenzoyl)-6-(2-methoxyphenyl)-1-methylpiperidine-2,4-dione
54. 3-(4-chloro-2-nitrobenzoyl)-6-(4-ethoxyphenyl)-1-methylpiperidine-2,4-dione 55. 3-(4-chloro-2-nitrobenzoyl)-6-(4-methylthiophenyl)-1-methylpiperidine-2,4-dione
56. 3-(4-chloro-2-nitrobenzoyl)-6-phenyl-1-methylpiperidine-2,4-dione
57. 3-(2,4-dinitrobenzoyl)piperidine-2,4-dione
58. 3-(5-chloro-2-nitrobenzoyl)piperidine-2,4-dione
59. 3-(2-nitrobenzoyl)piperidine-2,4-dione
60. 3-(2-chlorobenzoyl)piperidine-2,4-dione
61. 3-(3-trifluoromethylbenzoyl)piperidine-2,4-dione
62. 3-(2,4-dichlorobenzoyl)piperidine-2,4-dione
63. 3-(5-methyl-2-nitrobenzoyl)piperidine-2,4-dione
64. 3-(2,4-bistrifluoromethylbenzoyl)piperidine-2,4-dione
65. 3-(2-trifluoromethylbenzoyl)piperidine-2,4-dione
66. 3-benzoylpiperidine-2,4-dione
67. 3-(3,4-dichlorobenzoyl)piperidine-2,4-dione
68. 3-(2,5-dichlorobenzoyl)piperidine-2,4-dione
69. 3-(2-ethoxybenzoyl)piperidine-2,4-dione
70. 3-(2,3,4-trichlorobenzoyl)piperidine-2,4-dione
71. 3-(2,4,5-trichlorobenzoyl)piperidine-2,4-dione
72. 3-(4-bromo-2-nitrobenzoyl)piperidine-2,4-dione
73. 3-(4-cyano-2-nitrobenzoyl)piperidine-2,4-dione
74. 3-(2-nitro-4-trifluoromethylbenzoyl)piperidine-2,4-dione
75. 3-(4-fluoro-2-nitrobenzoyl)piperidine-2,4-dione
76. 3-(2-methyl-3-nitrobenzoyl)piperidine-2,4-dione
77. 3-(2-methyl-5-nitrobenzoyl)piperidine-2,4-dione
78. 3-(2-bromobenzoyl)piperidine-2,4-dione
79. 3-(2-methoxybenzoyl)piperidine-2,4-dione
80. 3-(3-nitrobenzoyl)piperidine-2,4-dione
81. 3-(3-bromobenzoyl)piperidine-2,4-dione
82. 3-(3-trifluoromethoxybenzoyl)piperidine-2,4-dione
83. 3-(3-methoxybenzoyl)piperidine-2,4-dione
84. 3-(3-chlorobenzoyl)piperidine-2,4-dione
85. 3-(3-methylbenzoyl)piperidine-2,4-dione
86. 3-(4-nitrobenzoyl)piperidine-2,4-dione
87. 3-(4-trifluoromethylbenzoyl)piperidine-2,4-dione
88. 3-(4-chlorobenzoyl)piperidine-2,4-dione
89. 3-(4-cyanobenzoyl)piperidine-2,4-dione
90. 3-(4-bromobenzoyl)piperidine-2,4-dione
91. 3-(4-methylbenzoyl)piperidine-2,4-dione
92. 3-(4-methoxybenzoyl)piperidine-2,4-dione
93. 3-(4-chloro-2-nitrobenzoyl)-5,6-dimethylpiperidine-2,4-dione
94. 3-(4-chloro-2-nitrobenzoyl)-6,6-pentamethylenepiperidine-2,4-dione
95. 3-(4-chloro-2-nitrobenzoyl)-5,5-dimethylpiperidine-2,4-dione
96. 3-(4-chloro-2-nitrobenzoyl)-1,5,5-trimethylpiperidine-2,4-dione
97. 3-(2,4-bistrifluoromethylbenzoyl)-6,6-dimethylpiperidine-2,4-dione
98. 3-(4-fluoro-2-nitrobenzoyl)-6,6-dimethylpiperidine-2,4-dione
99. 3-(2-nitro-4-trifluoromethylbenzoyl)-6,6-dimethylpiperidine-2,4-dione
100. 3-(2,3,4-trichlorobenzoyl)-6,6-dimethylpiperidine-2,4-dione
101. 3-(2,4,5-trichlorobenzoyl)-6,6-dimethylpiperidine-2,4-dione
102. 3-(4-bromo-2-nitrobenzoyl)-6,6-dimethylpiperidine-2,4-dione
103. 3-(4-methylsulphonyl-2-nitrobenzoyl)-6,6-dimethylpiperidine-2,4-dione
104. 2-(4-chloro-2-nitrobenzoyl)-5-phenylcyclohexane-1,3-dione
105. 4-carbethoxy-2-(4-chloro-2-nitrobenzoyl)-5-phenylcyclohexane-1,3-dione
106. 3-(2-nitro-4-trifluoromethylbenzoyl)-6-methyltetrahydropyran-2,4-dione
107. 3-(4-chloro-2-nitrobenzoyl)-6-phenyltetrahydropyran-2,4-dione
108. 2-(4-chloro-2-nitrobenzoyl)-5-(2-ethylthiopropyl)-6-carbethoxycyclohexane-1,3-dione
109. 3-(2-nitro-4-trifluoromethylbenzoyl)-6-methyl-6-trifluoromethylpiperidine-2,4-dione
110. 3-(4-methylsulphonyl-2-nitrobenzoyl)piperidine-2,4-dione
111. 6,6-dimethyl-3-(4-methoxy-2-nitrobenzoyl)piperidine-2,4-dione
112. 3-(4-fluoro-2-trifluoromethylbenzoyl)-6-phenylpiperidine-2,4-dione
113. 3-(2-chloro-4-trifluoromethylbenzoyl)-6-phenylpiperidine-2,4-dione
114. 3-(4-carbethoxy-2-nitrobenzoyl)-piperidine-2,4-dione
115. 3-(2-chloro-4-trifluoromethylbenzoyl)-piperidine-2,4-dione
116. 3-(4-fluoro-2-trifluoromethylbenzoyl)-piperidine-2,4-dione
117. 3-(2-nitro-4-trifluoromethylbenzoyl)-6-methylpiperidine-2,4-dione
118. 3-(2-nitro-4-trifluoromethylbenzoyl)-1,5,5-trimethylpiperidine-2,4-dione
119. 3-(4-methoxy-2-nitrobenzoyl)piperidine-2,4-dione
120. 3-(4-carbethoxy-2-nitrobenzoyl)-6,6-dimethylpiperidine-2,4-dione
121. 6,6-dimethyl-3-(4-methyl-2-nitrobenzoyl)piperidine-2,4-dione
122. 3-(4-tert-butylbenzoyl)piperidine-2,4-dione
123. 3-(4,5-dichloro-2-nitrobenzoyl)piperidine-2,4-dione
124. 3-(4-acetyl-2-nitrobenzoyl)piperidine-2,4-dione
125. 3-(4-methyl-2-nitrobenzoyl)piperidine-2,4-dione
126. 3-(2-chloro-4-methylsulphonylbenzoyl)piperidine-2,4-dione
127. 3-(4-chloro-5-methyl-2-nitrobenzoyl)piperidine-2,4-dione
128. 3-(2-chloro-5-nitrobenzoyl)piperidine-2,4-dione
129. 3-(4-bromo-2-methylbenzoyl)piperidine-2,4-dione
130. 3-(3-bromo-4-methylbenzoyl)piperidine-2,4-dione
131. 3-(2-methylthiobenzoyl)piperidine-2,4-dione
132. 3-(2-methylbenzoyl)piperidine-2,4-dione
133. 3-(4-iodobenzoyl)piperidine-2,4-dione
134. 3-(3,5-bistrifluoromethylbenzoyl)piperidine-2,4-dione
135. 3-(2-chloro-4-methylsulphonylbenzoyl)-6,6-dimethylpiperidine-2,4-dione
136. 6,6-dimethyl-3-(4-fluoro-2-trifluoromethylbenzoyl)piperidine-2,4-dione
137. 3-(4,5-dichloro-2-nitrobenzoyl)-6,6-dimethylpiperidine-2,4-dione
138. 3-(4-chloro-5-methyl-2-nitrobenzoyl)-6,6-dimethylpiperidine-2,4-dione
139. 3-(4-cyano-2-nitrobenzoyl)-6,6-dimethylpiperidine-2,4-dione
140. 3-(4-methylsulphonyl-2-nitrobenzoyl)-1,5,5-trimethylpiperidine-2,4-dione
141. 5-methyl-3-(2-nitro-4-trifluoromethylbenzoyl)-piperidine-2,4-dione
142. 5,5-dimethyl-3-(2-nitro-4-trifluoromethylbenzoyl)-piperidine-2,4-dione
143. 3-(2-nitro-4-trifluoromethylbenzoyl)-6,6-pentamethylenepiperidine-2,4-dione
144. 6-ethyl-6-methyl-3-(2-nitro-4-trifluoromethylbenzoyl)piperidine-2,4-dione 145. 6,6-diethyl-3-(2-nitro-4-trifluoromethylbenzoyl)-piperidine-2,4-dione
146. 3-(2-nitro-4-trifluoromethylbenzoyl)-1,6,6-trimethylpiperidine-2,4-dione
147. 3-(3,5-bistrifluoromethylbenzoyl)-6,6-dimethyl-piperidine-2,4-dione The numbers 1 to 147 are assigned to the above compounds for identification and reference hereinafter.

Compounds of general formula I of more particular interest are numbered, 104, 105, 106, 107, 109 and 1–10, 14, 20, 23–27, 34, 45–48, 53–76, 81–83, 94–100, 102, 103, 110, 111, 113 and 114–121.

According to a feature of the present invention, there is provided a method for controlling the growth of weeds (i.e. undesired vegetation) at a locus which comprises applying to the locus a herbicidally effective amount of at least one cyclic dione derivative of general formula I. For this purpose, the cyclic dione derivatives are normally used in the form of herbicidal compositions (i.e. in association with compatible diluents or carriers and/or surface active agents suitable for use in herbicidal compositions), for example as hereinafter described.

The compounds of general formula I show herbicidal activity against dicotyledonous (i.e. broad-leafed) and monocotyledonous (e.g. grass) weeds by pre- and/or, post-emergence application.

By the term "pre-emergence application" is meant application to the soil in which the weed seeds or seedlings are present before emergence of the weeds above the surface of the soil. By the term 'post-emergence application' is meant application to the aerial or exposed portions of the weeds which have emerged above the surface of the soil. For example, the compounds of general formula I may be used to control the growth of broad-leafed weeds, for example, *Aethusa cynapium, Abutilon theophrasti, Amaranthus retroflexus, Amsinckia intermedia, Anagallis arvensis, Anthemis arvensis, Atriplex patula, Bidens pilosa, Brassica nigra, Capsella bursa-pastoris, Chenopodium album, Chrysanthemum segetum, Cirsium arvense, Datura stramonium, Desmodium tortuosum, Emex australia, Euphorbia helioscopia, Fumaria officinalis, Galeopsis tetrahit, Galium aparine, Geranium dissectum, Ipomea purpurea, Lamium purpureum, Lapsana communis, Matricaria inodora, Monochoria vaginalis, Papaver rhoeas, Physalis longifolia, Plantago lanceolata,* Polygonum spp., (e.g. *Polygonum lapathifolium, Polygonum aviculare, Polygonum convolvulus* and *Polygonum persicaria*), Portulaca oleracea, Raphanus raphanistrum, Rotala indica, Rumex obtusifolius, Saponaria vaccaria, Scandix pecten-veneris, Senecio vulgaris, Sesbania florida, Sida spinosa, Silene alba, Sinapis arvensis, Solanum nigrum, Sonchus arvensis, Spergula arvensis, Stellaria media, Thlaspi arvense, Tribulus terrestria, Urtica urens, Veronica hederifolia, Veronica persica, Viola arvensis and *Xanthium strumarium,* and grass weeds, for example, *Alopecurus myosuroides, Apera spica-venti, Agrostis stolonifera, Avena fatua, Avena ludoviciana,* Brachiaria spp., *Bromus sterilis, Bromus tectorum,* Cenchrus spp., *Cynodon dactylon, Digitaria sanquinalis, Echinochloa crus-galli, Eleusine indica, Setaria viridis* and *Sorghum halepense* and sedges, for example *Cyperus esculentus, Cyperus iria* and *Cyperus rotundus,* and *Eleocharis acicularis.*

The amounts of compounds of general formula I applied vary with the nature of the weeds, the compositions used, the time of application, the climatic and edaphic conditions and (when used to control the growth of weeds in crop-growing areas) the nature of the crops. When applied to a crop-growing area, the rate of application should be sufficient to control the growth of weeds without causing substantial permanent damage to the crop. In general, taking these factors into account, application rates between 0.01 kg and 20 kg of active material per hectare give good results. However, it is to be understood that higher or lower application rates may be used, depending upon the particular problem of weed control encountered.

The compounds of general formula I may be used to control selectively the growth of weeds, for example to control the growth of those species hereinbefore mentioned, by pre- or post-emergence application in a directional or non-directional fashion, e.g. by directional or non-directional spraying, to a locus of weed infestation which is an area used, or to be used, for growing crops, for example cereals, e.g. wheat, barley, oats, maize and rice, soya beans, field and dwarf beans, peas, lucerne, cotton, peanuts, flax, onions, carrots, cabbage, oilseed rape, sunflower, sugar beet, and permanent or sown grassland before or after sowing of the crop or before or after emergence of the crop. For the selective control of weeds at a locus of weed infestation which is an area used, or to be used, for the growing of crops, e.g. the crops hereinbefore mentioned, application rates between 0.01 kg and 8.0 kg, and preferably between 0.01 kg and 4.0 kg, of active material per hectare are particularly suitable.

The compounds of general formula I may also be used to control the growth of weeds, especially those indicated above, by pre- or post-emergence application in established orchards and other tree-growing areas, for example forests, woods and parks, and plantations e.g. sugar cane, oil palm and rubber plantations. For this purpose they may be applied in a directional or non-directional fashion (e.g. by directional or non-directional spraying) to the weeds or to the soil in which they are expected to appear, before or after planting of the trees or plantations at application rates between 0.25 kg and 10.0 kg, and preferably between 0.5 kg and 8.0 kg, of active material per hectare.

The compounds of general formula I may also be used to control the growth of weeds, especially those indicated above, at loci which are not crop-growing areas but in which the control of weeds is nevertheless desirable. Examples of such non-crop-growing areas include airfields, industrial sites, railways, roadside verges, the verges of rivers, irrigation and other waterways, scrublands and fallow or uncultivated land, in particular where it is desired to control the growth of weeds in order to reduce fire risks. When used for such purposes in which a total herbicidal effect is frequently desired, the active compounds are normally applied at dosage rates higher than those used in crop-growing areas as hereinbefore described. The precise dosage will depend upon the nature of the vegetation treated and the effect sought. Pre- or post-emergence application, and preferably pre-emergence application, in a directional or non-directional fashion (e.g. by directional or non-directional spraying) at application rates between 1.0 kg and 20.0 kg, and preferably between 5.0 and 10.0 kg, of active material per hectare are particularly suitable for this purpose.

When used to control the growth of weeds by pre-emergence application, the compounds of general formula I may be incorporated into the soil in which the weeds are expected to emerge. It will be appreciated that when the compounds of general formula I are used to control the growth of weeds by post-emergence application, i.e. by application to the aerial or exposed portions of emerged weeds, the compounds of general formula I will also normally come into contact with the soil and may also then exercise a pre-emergence control on later-germinating weeds in the soil.

Where especially prolonged weed control is required, the application of the compounds of general formula I may be repeated if required.

According to a further feature of the present invention, there are provided compositions suitable for herbicidal use comprising one or more of the cyclic dione derivatives of general formula I in association with, and preferably homogeneously dispersed in, one or more compatible herbicidally-acceptable diluents or carriers and/or surface active agents (i.e. diluents or carriers and/or surface active agents of the type generally accepted in the art as being suitable for use in herbicidal compositions and which are compatible with compounds of general formula I). The term "homogeneously dispersed" is used to include compositions in which the compounds of general formula I are dissolved in the other components. The term "herbicidal compositions" is used in a broad sense to include not only compositions which are ready for use as herbicides but also concentrates which must be diluted before use. Preferably, the compositions contain from 0.05 to 90% by weight of one or more compounds of general formula I.

The herbicidal compositions may contain both a diluent or carrier and surface-active (e.g. wetting, dispersing, or emulsifying) agent. Surface-active agents which may be present in herbicidal compositions of the present invention may be of the ionic or non-ionic types, for example sulphoricinoleates, quaternary ammonium derivatives, products based on condensates of ethylene oxide with alkyl and polyaryl phenols, e.g. nonyl- or octyl-phenols, or carboxylic acid esters of anhydrosorbitols which have been rendered soluble by etherification of the free hydroxy groups by condensation with ethylene oxide, alkali and alkaline earth metal salts of sulphuric acid esters and sulphonic acids such as dinonyl- and dioctyl-sodium sulphonosuccinates and alkali and alkaline earth metal salts of high molecular weight sulphonic acid derivatives such as sodium and calcium lignosulphonates and sodium and calcium alkylbenzene sulphonates.

Suitably, the herbicidal compositions according to the present invention may comprise up to 10%, e.g. from 0.05% to 10%, of surface-active agent but, if desired, herbicidal compositions according to the present invention may comprise higher proportions of surface-active agent, for example up to 15% in liquid emulsifiable suspension concentrates and up to 25% in liquid water soluble concentrates.

Examples of suitable solid diluents or carriers are aluminum silicate, talc, calcined magnesia, kieselguhr, tricalcium phosphate, powdered cork, adsorbent carbon black and clays such as kaolin and bentonite. The solid compositions (which may take the form of dusts, granules or wettable powders) are preferably prepared by grinding the compounds of general formula I with solid diluents or by impregnating the solid diluents or carriers with solutions of the compounds of general formula I in volatile solvents, evaporating the solvents and, if necessary, grinding the products so as to obtain powders. Granular formulations may be prepared by absorbing the compounds of general formula I (dissolved in suitable solvents, which may, if desired, be volatile) onto the solid diluents or carriers in granular form and, if desired, evaporating the solvents, or by granulating compositions in powder form obtained as described above. Solid herbicidal compositions, particularly wettable powders and granules, may contain wetting or dispersing agents (for example of the types described above), which may also, when solid, serve as diluents or carriers.

Liquid compositions according to the invention may take the form of aqueous, organic or aqueous-organic solutions, suspensions and emulsions which may incorporate a surface-active agent. Suitable liquid diluents for incorporation in the liquid compositions include water, glycols, tetrahydrofurfuryl alcohol, acetophenone, cyclohexanone, isophorone, toluene, xylene, mineral, animal and vegetable oils and light aromatic and naphthenic fractions of petroleum (and mixtures of these diluents). Surface-active agents, which may be present in the liquid compositions, may be ionic or non-ionic (for example of the types described above) and may, when liquid, also serve as diluents or carriers.

Powders, dispersible granules and liquid compositions in the form of concentrates may be diluted with water or other suitable diluents, for example mineral or vegetable oils, particularly in the case of liquid concentrates in which the diluent or carrier is an oil, to give compositions ready for use. When desired, liquid compositions of the compound of general formula I may be used in the form of self-emulsifying concentrates containing the active substances dissolved in the emulsifying agents or in solvents containing emulsifying agents compatible with the active substances, the simple addition of water to such concentrates producing compositions ready for use.

Liquid concentrates in which the diluent or carrier is an oil may be used without further dilution using the electrostatic spray technique.

Herbicidal compositions according to the present invention may also contain, if desired, conventional adjuvants such as adhesives, protective colloids, thickeners, penetrating agents, stabilisers, sequestering agents, anti-caking agents, colouring agents and corrosion inhibitors. These adjuvants may also serve as carriers or diluents.

Preferred herbicidal compositions according to the present invention are aqueous suspension concentrates which comprise from 10 to 70% of one or more compounds of general formula I, from 2 to 10% of surface-active agent, from 0.1 to 5% w/v (weight/volume) of thickener and from 15 to 87.9% by volume of water; wettable powders which comprise from 10 to 90% w/w (weight/weight) of one or more compounds of general formula I, from 2 to 10% w/w of surface-active agent and from 8 to 88% w/w of solid diluent or carrier; soluble powders which comprise from 10 to 90% w/w (weight/weight) of one or more compounds of general formula I, from 2 to 40% w/w of sodium carbonate and from 0 to 88% w/w of solid diluent; liquid water soluble concentrates which comprise from 5 to 50%, e.g. 10 to 30%, w/v of one or more compounds of general formula I, from 5 to 25% w/v of surface-active agent and from 25 to 90%, e.g. 45 to 85%, by volume of water-miscible solvent, e.g. dimethylformamide, or a mixture of water-miscible solvent and water; liquid emulsifiable suspension concentrates which comprise from 10 to 70% w/v of one or more compounds of general formula I, from 5 to 15% w/v of surface-active agent, from 0.1 to 5% w/v of thickener and from 10 to 84.9% by volume of organic solvent; granules which comprise from 1 to 90%, e.g. 2 to 10%, w/w of one or more compounds of general formula I, from 0.5 to 7%, e.g. 0.5 to 2%, w/w of surface-active agent and from 3 to 98.5%, e.g. 88 to 97.5%, w/w of granular carrier and emulsifiable concentrates which comprise 0.05 to 90% w/v, and preferably from 1 to 60% w/v of one or more compounds of general formula I, from 0.01 to 10% w/v, and preferably from 1 to 10% w/v, of surface-active agent and from 9.99 to 99.94%, and preferably from 39 to 98.99%, by volume of organic solvent.

Herbicidal compositions according to the present invention may also comprise the compounds of general formula I in association with, and preferably homogeneously dispersed in, one or more other pesticidally active compounds and, if desired, one or more compatible pesticidally acceptable diluents or carriers, surface-active agents and conventional adjuvants as hereinbefore described. Examples of other pesticidally active compounds which may be included in, or used in conjunction with, the herbicidal compositions of the present invention include herbicides, for example to increase the range of weed species controlled, for example alachlor [2-chloro-2',6'-diethyl-N-(methoxymethyl)acetanilide], asulam [methyl(4-aminobenzenesulphonyl)carbamate], alloxydim Na [sodium salt of 2-(1-allyloxyaminobutylidene)-5,5-dimethyl-4-methoxycarbonylcyclohexane-1,3-dione], atrazine [2-chloro-4-ethylamino-6-isopropylamino-1,3,5-triazine], barban [4-chlorobut-2-ynyl N-(3-chlorophenyl)carbamate], benzoylprop-ethyl [ethyl N-benzoyl-N-(3,4-dichlorophenyl-2-aminopropionate], bromoxynil [3,5-dibromo-4-hydroxybenzonitrile], butachlor [N-(butoxymethyl)-2-chloro-2',6'-diethylacetanilide], butylate [S-ethyl N,N-diisobutyl(thiocarbamate)], carbetamide [D-N-ethyl-2-(phenylcarbamoxyloxy)propionamide], chlorfenprop-methyl [methyl 2-chloro-3-(4-chlorophenyl)propionate], chlorpropham [isopropyl N-(3-chlorophenyl)carbamate], chlortoluron [N'-(3-chloro-4-methylphenyl)-N,N-dimethylurea], cyanazine [2-chloro-4-(1-cyano-1-methylethylamino)-6-ethylamino-1,3,5-triazine], cycloate [N'-cyclohexyl-N-ethyl-S-ethyl(thiocarbamate)], 2,4-D [2,4-dichlorophenoxyacetic acid], dalapon [2,2-dichloropropionic acid], 2,4-DB [4-(2,4-dichlorophenoxy)butyric acid], desmedipham [3-(ethoxycarbonylamino)phenyl N-phenyl-carbamate], diallate [S-2,3-dichloroallyl-N,N-di-isopropyl(thiocarbamate)], dicamba [3,6-dichloro-2-methoxybenzoic acid], dichlorprop [($\pm$)-2-(2,4-dichlorophenoxy)propionic acid], difenzoquat [1,2-dimethyl-3,5-diphenyl-pyrazolium salts], dimefuron 4-[2-chloro-4-(3,3-dimethylureido)phenyl]-2-t-butyl-1,3,4-oxadiazolin-5-one, dinitramine [$N^1,N^1$-diethyl-2,6-dinitro-4-trifluoromethyl-m-phenylenediamine], diuron [N'-(3,4-dichlorophenyl)-N,N-dimethylurea], EPTC [S-ethyl N,N-dipropyl(thiocarbamate)], ethofumesate [2-ethoxy-2,3-dihydro-3,3-dimethylbenzofuran-5-yl methylsulphonate], flampropisopropyl [isopropyl ($\pm$)-2-(N-benzoyl-3-chloro-4-fluoroanilino)propionate], flampropmethyl [methyl ($\pm$)-2-(N-benzoy-3-chloro-4-fluoroanilino)propionate], fluometuron [N'-(3-trifluoromethylphenyl)-N,N-dimethylurea], ioxynil [4-hydroxy-3,5-di-iodobenzonitrile], isoproturon [N'-(4-isopropylphenyl)-N,N-dimethylurea], linuron [N-(3,4-dichlorophenyl-N-methoxy-N-methylurea], MCPA [4-chloro-2-methylphenoxyacetic acid, MCPB [4-(4-chloro-2-methylphenoxy)butyric acid], mecoprop [($\pm$)-2-(4-chloro-2-methylphenoxy)propionic acid], metamitron [4-amino-3-methyl-6-phenyl-1,2,4-triazin-5(4H)one], methabenzthiazuron [N-(benzothiazol-2-yl)-N,N'-dimethylurea], metribuzin [4-amino-6-t-butyl-3-(methylthio)-1,2,4-triazin-5(4H)-one], molinate [S-ethyl N,N-hexamethylene(thiocarbamate)], oxadiazon [3-(2,4-dichloro-5-isopropoxyphenyl)-5-t-butyl-1,3,4-oxadiazolin-2-one], paraquat [1,1'-dimethyl-4,4'-bipyridylium salts], pebulate [S-propyl N-butyl-N-ethyl(thiocarbanate)], phenmedipham [3-(methoxycarbonylamino)phenyl N-(3-methylphenyl)carbamate], prometryne [4,6-bisisopropylamino-2-methylthio-1,3,5-triazine], propachlor [2-chloro-N-isopropylacetanilide], propanil [N-(3,4-dichlorophenyl)propionamide], propham [isopropyl N-phenylcarbamate], pyrazone [5-amino-4-chloro-2-phenylpyridazin-3(2H)-one], simazine [2-chloro-4,6-bisethylamino-1,3,5-triazine], TCA (trichloroacetic acid), thiobencarb [S-(4-chlorobenzyl)-N,N-diethylthiolcarbamate], tri-allate [S-2,3,3-trichloroallyl N,N-di-isopropyl(thiocarbamate)] and trifluralin [2,6-dinitro-N,N-dipropyl-4-trifluoromethylaniline]; insecticides, e.g. carbaryl [naphth-1-yl N-methylcarbamate]; synthetic pyrethroids, e.g. permethrin and cypermethrin; and fungicides, e.g. 2,6-dimethyl-4-tridecyl-morpholine, methyl N-(1-butylcarbamoyl-benzimidazol-2-yl)carbamate, 1,2-bis(3-methoxycarbonyl-2-thioureido)benzene, isopropyl 1-carbamoyl-3-(3,5-dichlorophenyl)hydantoin and 1-(4-chloro-phenoxy)-3,3-dimethyl-1-(1,2,4-triazol-1-yl)-butan-2-one. Other biologically active materials which may be included in, or used in conjunction with, the herbicidal compositions of the present invention are plant growth regulators, e.g. succinamic acid, (2-chloroethyl)trimethylammonium chloride and 2-chloroethane-phosphonic acid; or fertilizers, e.g. containing nitrogen, potassium and phosphorus and trace elements known to be essential to successful plant life, e.g. iron, magnesium, zinc, maganese, cobalt and copper.

Pesticidally active compounds and other biologically active materials which may be included in, or used in conjunction with, the herbicidal compositions of the present invention, for example those hereinbefore mentioned, and which are acids, may, if desired, be utilized in the form of conventional derivatives, for example alkali metal and amine salts and esters.

According to a further feature of the present invention there is provided an article of manufacture comprising at least one of the cyclic dione derivatives of general formula I or, as is preferred, a herbicidal composition as hereinbefore described, and preferably a herbicidal concentrate which must be diluted before use, comprising at least one of the cyclic dione derivatives of general formula I within a container for the aforesaid derivative or derivatives of general formula I, or a said herbicidal composition, and instructions physically associated with the aforesaid container setting out the manner in which the aforesaid derivative or derivatives of general formula I or herbicidal composition contained therein is to be used to control the growth of weeds. The containers will normally be of the types conventionally used for the storage of chemical substances which are solid at normal ambient temperatures and herbicidal compositions particularly in the form of concentrates, for example cans and drums of metal, which may be internally-lacquered, and plastics materials, bottles of glass and plastics materials and, when the contents of the container is a solid, for example granular, herbicidal compositions, boxes, for example of cardboard, plastics materials and metal, or sacks. The containers will normally be of sufficient capacity to contain amounts of the cyclic dione derivative or herbicidal compositions sufficient to treat at least one acre of ground to control the growth of weeds therein but will not exceed a size which is convenient for conventional methods of handling. The instructions will be physically associated with the container, for example by being printed directly thereon or on a label or tag affixed thereto. The directions will normally indicate that the contents of the container, after dilution if necessary, are to be applied to control the growth of weeds at rates of application between 0.01 kg and 20 kg of active material per hectare in the manner and for the purposes hereinbefore described.

In experiments on herbicidal activity carried out on representative compounds of general formula I, the following results have been obtained:

TEST METHOD

Weed Control Test a) General

Appropriate quantities of the test compounds Nos. 1 to 123 were dissolved in acetone to give solutions equivalent to an application rate of 1000 g of test compound per hectare (g/ha) (except for compounds 4 and 105 for which an application rate equivalent to 2000 g/ha was used). These solutions were applied from a standard laboratory herbicide sprayer using a flat fan jet travelling at 1.8 m.p.h. (2.9 km/hr), and delivering the equivalent of 540 liters of spray fluid per hectare.

b) Weed Control: Pre-emergence application

Weed seeds were sown on the surface of John Innes No. 1 potting compost (7 parts by volume of sterilised loam, 3 parts by volume of peat and 2 parts by volume of fine grit) in 70 mm square, 75 mm deep plastic pots. The quantities of seed per pot were as follows:

| Weed species | Approximate number seeds/pot |
| --- | --- |
| 1) Broad-leafed weeds | |
| Abutilon theophrasti | 10 |
| Sinapis arvensis | 20 |
| Chenopodium album | 60 |
| Ipomoea purpurea | 10 |
| 2) Grass-weeds | |
| Avena fatua | 15 |
| Echinochloa crus-galli | 20 |
| 3) Sedges | |
| Cyperus esculentus | 3 |

The test compounds were applied to the uncovered seeds as described in (a) above and the seeds were covered with 25 ml of sharp sand after spraying. A single pot of each weed species was allocated to each treatment with unsprayed controls and controls sprayed with acetone alone. After treatment, the pots were kept in the greenhouse and were watered overhead. Visual assessment of weed control activity was made 17–20 days after spraying. The results were expressed as the percentage reduction in growth or kill of the weeds, in comparison with the plants in the control pots. The results obtained are presented below.

c) Weed control: Post-emergence application

Weed species were grown and then transplanted at the seedling stage into John Innes No. 1 potting compost in 70 mm square, 75 mm deep plastic pots, except for *Avena fatua*, which was sown directly in the test pot and not transplanted. The plants were then grown in the greenhouse until ready for spraying with the test compounds. The number of plants per pot, and the growth of the plant at spraying were as follows:

| Weed Species | Number of plants per pot | Growth stages at spraying |
| --- | --- | --- |
| 1) Broad-leafed weeds | | |
| Abutilon theophrasti | 3 | 1–2 leaves |
| Sinapis arvensis | 4 | 2 leaves |
| Chenopodium album | 4 | 2–4 leaves |
| Ipomoea purpurea | 3 | 1–2 leaves |
| 2) Grass weeds | | |
| Avena fatua | 15 | 1–2 leaves |
| Echinochloa crus-galli | 4 | 2–3 leaves |
| 3) Sedges | | |
| Cyperus esculentus | 3 | 3 leaves |

The test compounds were applied to the plants as described in (a) above. A single pot of each weed species was allocated to each treatment, with unsprayed controls and controls sprayed with acetone alone. After spraying, the pots were watered overhead, commencing 24 hours after spraying. Visual assessment of the control of the growth of the weeds was made 17–20 days after spraying. The results were expressed as the percentage reducting in growth or kill of the weeds, in comparison with the plants in the control pots. The results obtained are presented below.

RESULTS

In the pre-emergence test the following compounds gave 100% control of *Chenopodium album* and between 10 and 100% control of the other species: 1, 3, 4, 6, 7, 8, 10, 20, 34, 56, 59, 62, 63, 64, 70, 72, 73, 74, 75, 76, 95, 96, 97, 98, 99, 100, 102, 103, 104, 105, 106, 109, 110, 113, 114, 115, 116, 117, 118, 119, 120 and 121.

Other compounds gave between 10 and 100% control of some but not all the species.

In the post emergence test the following compounds gave 100% control of *Chenopodium album* and between 10 and 100% control of the other species: 1, 2, 3, 4, 5, 6, 7, 8, 9, 10, 14, 20, 23, 24, 25, 26, 27, 34, 45, 46, 47, 48, 53, 54, 55, 56, 57, 58, 59, 60, 61, 62, 63, 64, 65, 66, 67, 68, 69, 70, 71, 72, 73, 74, 75, 76, 81, 82, 83, 94, 95, 96, 97, 98, 99, 100, 102, 103, 104, 106, 109, 110, 111, 113, 114, 115, 116, 117, 118, 119, 120 and 121.

Other compounds gave between 10 and 100% control of some but not all the species.

The following examples illustrate herbicidal compositions according to the present invention:

EXAMPLE 1

A wettable powder was formed from:

| | |
| --- | --- |
| 3-(2-nitrobenzoyl)-6-phenylpiperidine-2,4-dione | 50% w/w |
| Ethylan BCP (a nonylphenol/ethylene oxide condensate containing 9 moles of ethylene oxide per mol of phenol) | 5% w/w |
| Aerosil (silicon dioxide of microfine particle size) | 5% w/w |
| Celite PF (synthetic magnesium silicate carrier) | 40% w/w | by absorbing the Ethylan BCP onto the Aerosil, mixing with the other ingredients and grinding the mixture in a hammer-mill to give a wettable powder.

Similar wettable powders may be prepared as described above by replacing the 3-(2-nitrobenzoyl)-6-phenylpiperidine-2,4-dione by other compounds of general formula I.

EXAMPLE 2

An aqueous suspension concentrate was formed from:

| | |
|---|---|
| 3-(2-nitrobenzoyl)-6-phenylpiperidine-2,4-dione | 50% w/v |
| Ethylan BCP | 1.0% w/v |
| Sopropon T36 (sodium salt of polycarboxylic acid) | 0.2% w/v |
| Ethylene glycol | 5% w/v |
| Rhodigel 23 (polysaccharide xanthan gum thickener) | 0.15% w/v |
| distilled water to | 100% by volume | by intimately mixing the ingredients and grinding in a ball-mill for 24 hours.

Similar aqueous concentrates may be prepared as described above by replacing the 3-(2-nitrobenzoyl)-6-phenylpiperidine-2,4-dione by other compounds of general formula I.

EXAMPLE 3

A soluble powder was formed from:

| | |
|---|---|
| 3-(2-nitrobenzoyl)-6-phenylpiperidine-2,4-dione | 60% w/w |
| Sodium carbonate | 40% w/w | by mixing the ingredients and grinding the mixture in a hammer-mill to give a soluble powder.

Similar soluble powders may be prepared as described above by replacing the 3-(2-nitrobenzoyl)-6-phenylpiperidine-2,4-dione by other compounds of general formula I.

The compounds of general formula I can be prepared by the application or adaptation of known methods (i.e. methods heretofore used or described in the chemical literature), for example as hereinafter identified.

According to a feature of the present invention, the compounds of general formula I may be prepared by the reaction of a compound of general formula II with the appropriate benzoic acid or a reactive derivative thereof, for example the benzoyl cyanide, chloride or anhydride, or for example an N-benzoyl-aromatic heterocycle such as the N-benzoylimidazole.

The reaction of the compound of general formula II with the benzoyl cyanide or the N-benzoylimidazole is generally performed in the presence of zinc chloride and triethylamine in an inert organic solvent such as dichloromethane.

The reaction of the compound of general formula II with the benzoic acid or benzoyl chloride is generally performed in the presence of diethyl cyanophosphate and triethylamine in an inert organic solvent such as dimethylformamide or in the presence of 1,5-diazabicyclo[5,4,0]undecene-5 in an inert organic solvent such as toluene at the reflux temperature of the reaction mixture.

According to a further feature of the present invention, the compounds of general formula I may be prepared by the rearrangement of a compound of general formula III, optionally prepared in situ, using a source of cyanide ion or in the presence of aluminium chloride or a 4-(substituted amino)pyridine, for example 4-dimethylaminopyridine.

The source of cyanide ion may be acetone cyanohydrin, hydrogen cyanide, trimethylsilyl cyanide or zinc cyanide in the presence of triethylamine in an inert organic solvent such as dichloromethane or acetonitrile.

The rearrangement using aluminium chloride may be performed in an inert organic solvent such as 1,2-dichloroethane at ambient temperature.

The rearrangement using a 4-(substituted amino)pyridine may be performed in an inert organic solvent such as toluene at the reflux temperature of the reaction mixture.

Compounds of general formula III may be prepared by benzoylation of a compound of general formula II using a benzoyl halide. The compounds of general formula III and their preparation constitute features of the present invention.

Compounds of general formula II wherein X represents a group $-NR^4-$ and Y represents a methylene group $-C(R^5)(R^6)-$ may be prepared by the hydrolysis and decarboxylation of a compound of general formula IV or by the reaction of a compound of general formula V with a diketene.

Compounds of general formula II which are new, and their preparation constitute features of the present invention. Novel compounds of general formula II which are of particular interest are those in which:

Y represents a methylene group $-CR^5R^6-$ and (a) X represents a group $-NR^4-$ as hereinbefore defined and $R^1$ and $R^2$ are as hereinbefore defined with the proviso that $R^1$, $R^2$ and $R^4$ do not simultaneously represent hydrogen atoms;

(b) X represents the methylene group, $R^2$ represents a cycloalkyl group containing from 3 to 6 carbon atoms and $R^1$ is as hereinbefore defined;

(c) X represents the oxygen atom, $R^2$ represents a straight- or branched-chain alkyl group containing from 1 to 6 carbon atoms which is substituted by one or more halogen atoms or represents a cycloalkyl group containing from 3 to 6 carbon atoms and $R^1$ is as hereinbefore defined or $R^1$ and $R^2$ together represent an alkylene group containing from 2 to 6 carbon atoms; or (d) X represents the sulphur atom, $R^2$ represents a straight- or branched-chain alkyl group containing from 1 to 6 carbon atoms which is substituted by one or more halogen atoms and $R^1$ is as hereinbefore defined or $R^1$ and $R^2$ together represent an alkylene group containing from 2 to 6 carbon atoms.

Compounds of formula II as defined in (a) may be prepared as hereinbefore described.

Compounds of formula II as defined in (b) may be prepared by treating the corresponding 4-alkoxycarbonyl-5-cycloalkyl-cyclohexane-1,3-dione with an aqueous solution of an alkali metal hydroxide, e.g. sodium hydroxide in the presence of an alkanol at a temperature from 0° C. to the reflux temperature of the reaction mixture followed by acidification with for example aqueous hydrochloric acid.

Compounds of formula II as defined in (c) may be prepared by treating the corresponding δ-hydroxy-β-ketoester of formula $R^1R^2C(OH)C(R^5)(R^6)C(=O)CH_2CO_2$ alkyl, wherein the various symbols are as hereinbefore defined, with an aqueous solution of an alkali metal hydroxide, e.g. sodium hydroxide at a temperature from 0° C. to 50° C. followed by acidification with for example aqueous hydrochloric acid.

Compounds of formula II as defined in (d) may be prepared by treating the corresponding 4-oxo tetrahydrothiopyranthione with aqueous hydrogen peroxide in an inert organic solvent, e.g. ethanol, in the presence of an alkali metal hydroxide, e.g. potassium hydroxide at a temperature from −30° C. to 30° C.

Other compounds of general formula II are known or can be prepared by the application or adaptation of known methods. By the expression "known methods" as used in this specification is meant methods heretofore used or described in the literature.

Compounds of general formula IV may be prepared by cyclisation of a compound of general formula VI wherein $R^9$ represents a straight- or branched-chain alkyl group containing from 1 to 6 carbon atoms and $R^{10}$ represents a straight- or branched-chain alkyl group containing from 1 to 6 carbon atoms.

The reaction may be effected in the presence of an alkali metal alkoxide in the corresponding alcohol e.g. sodium ethoxide in ethanol.

Compounds of general formula VI may be prepared by the reaction of a compound of general formula VII with an acid of general formula VIII or a reactive derivative of the acid e.g. the acyl halide, or by the reaction of the corresponding hydroxy compound with an acyl nitrile.

Compounds of general formula VII wherein $R^2$ represents a phenyl group and $R^4$ represents an alkyl group may be prepared by hydrogenating a N-methyl-3-phenylisoxazolidine-3-one.

Compounds of general formula IV wherein $R^1$ and $R^6$ represent hydrogen atoms may also be prepared by catalytic hydrogenation, using for example platinum oxide or palladium on charcoal, of a compound of general formula IX.

Compounds of general formula IX may be prepared in a similar manner to that hereinbefore described for the preparation of compounds of general formula IV.

Salts with agriculturally acceptable bases of compounds of general formula I may be prepared from the corresponding compounds of general formula I by methods known per se, for example by reacting stoichiometric quantities of the compounds of general formula I and the appropriate base, for example, an alkali metal hydroxide, carbonate or bicarbonate, an alkaline earth metal hydroxide or carbonate, ammonia or an amine (e.g. diethanolamine, triethanolamine, octylamine, morpholine or dioctylamine), in a suitable solvent. Acid addition salts of compounds of general formula I which incorporate an amino radical may be prepared from the corresponding compounds of general formula I by methods known per se, for example by reacting stoichiometric quantities of the compound of general formula I and the appropriate acid, for example an inorganic acid, e.g. hydrochloric acid, sulphuric acid, phosphoric acid or nitric acid, or an organic acid, e.g. acetic acid, in a suitable solvent. The salts may, if necessary, be purified by recrystallisation from one, two or more suitable solvents.

As well as being useful in themselves as herbicidally active compounds, salts of compounds of general formula I may also be used in the purification of the corresponding compounds of general formula I, for example by exploitation of the solubility difference between the salts and the parent compounds in water and in organic solvents, by techniques which are well known to those skilled in the art.

It will be understood by those skilled in the art that in the performance of the processes described above of the present invention it may be desirable to introduce chemical protecting groups into the reactants in order to avoid secondary reactions taking place, for example in the methods of preparation of derivatives hereinbefore described hydroxy substituent(s) within the definition of the groups $R^3$ as defined in relation to general formula I may have been converted into benzyloxy groups before reaction as described with subsequent removal of the protecting benzyl groups.

It is to be understood that the amino, carboxy and hydroxy groups which are present in certain reactants may be protected by any protective groups which are usually employed for protecting amines, carboxylic acids or alcohols, and whose use does not adversely affect the remainder of the molecule.

By way of examples, the amino group can be protected by radicals such as tert-butoxycarbonyl, 2,2,2-trichloroethoxycarbonyl, trichloroacetyl, trityl, benzyl, dibenzyl, benzyloxycarbonyl, p-nitrobenzyloxycarbonyl, p-methoxybenzyloxycarbonyl, chloroacetyl, or trifluoroacetyl, the carboxy groups can be protected by radicals such as methoxymethyl, tert-butyl, benzhydryl, p-nitrobenzyl or p-methoxybenzyl, and the hydroxy groups can be protected by radicals such as benzyl, trityl, tetrahydropyranyl or 2-methoxy-prop-2-yl.

The various protective radicals can be removed simultaneously or successively.

By way of example,

1. The removal of the protective groups of amines is effected as follows:

in the case of a tert-butoxycarbonyl, trityl or p-methoxybenzyloxycarbonyl radical, by treatment in an acid medium. Preferably, trifluoroacetic acid is used and the process is carried out at a temperature of between 0° and 20° C., or anhydrous or aqueous formic acid, or para-toluenesulphonic or methanesulphonic acid, is used in acetone or acetonitrile at a temperature between 20° C. and the reflux temperature of the reaction mixture. Under these conditions, the compound of general formula I can be obtained in the form of the trifluoroacetate, the solvate with formic acid, the methanesulphonate or the para-toluenesulphonate, and from these the amine group can be liberated by any method which is in itself known for obtaining an amine from one of its salts without affecting the remainder of the molecule. In particular, the process is carried out by bringing the compound into contact with an ion exchange resin or by the action of an organic base.

In the case of a 2,2,2-trichloroethoxycarbonyl or p-nitrobenzyloxycarbonyl radical, by reduction (especially by treatment with zinc in acetic acid).

In the case of a chloroacetyl or trichloroacetyl radical, by applying the method described in the British Patent published under No. 1,454,589.

In the case of a benzyl, dibenzyl or benzyloxycarbonyl radical, by catalytic hydrogenation.

In the case of a trifluoroacetyl radical, by treatment in a basic medium.

2. The removal of the protective groups from the carboxy radical is effected as follows:

in the case of a tert-butyl, p-methoxybenzyl or benzhydryl radical, by treatment in an acid medium, under the conditions described above for the removal of the protective trityl radical from an amino group. In the case of the benzhydryl radical, the process can be carried out in the presence of anisole.

In the case of a methoxymethyl group, by treatment in a dilute acid medium.

In the case of a p-nitrobenzyl group, by reduction (especially by treatment with zinc in acetic acid, or by hydrogenolysis).

3. The removal of the protective groups from the hydroxy radicals is effected as follows:

in the case of a benzyl, trityl or tetrahydropyranyl group, by acidolysis, for example with trifluoroacetic acid, aqueous or non-aqueous formic acid or para-toluenesulphonic acid.

In the case of the 2-methoxy-prop-2-yl-group, in accordance with the method described in British Patent No. 2021561.

It will be understood that it may be desirable to change the nature of one or more of the substituents at an appropriate stage during the synthesis of the compounds of the invention, for example, the compounds of general formula I wherein $R^3$ represents an amino group may be alternatively prepared from the corresponding compounds of general formula I wherein $R^3$ represents a nitro group by the application or adaptation of known methods for such conversion. Compounds of general formula I wherein $R^3$ represents an amino group may be transformed to diazonium salts, which are useful in synthesis as described in Morrison and Boyd's "Organic Chemistry" (1959), and thence to, for example, an iodine atom.

The following examples and reference examples illustrate the preparation of compounds according to the present invention.

EXAMPLE 4

Compound 1

A solution of 4-chloro-2-nitrobenzoyl chloride (4.4 g) in dry dichloromethane (5 ml) was added at 5°–10° C. to a stirred solution of 6,6-dimethylpiperidine-2,4-dione (2.8 g) and triethylamine (2.8 ml) in dry dichloromethane (50 ml) and the mixture was stirred at ambient temperature for 18 hours. Triethylamine (8.4 ml) and acetone cyanohydrin (0.4 ml) were added successively to the solution and the mixture was stirred at ambient temperature for 4 hours. The resulting solution was washed successively with 2N hydrochloric acid (25 ml) and water (3×25 ml), dried over sodium sulphate and evaporated under reduced pressure to give a yellow solid which was recrystallised from acetonitrile to give 3-(4-chloro-2-nitrobenzoyl)-6,6-dimethylpiperidine-2,4-dione (4 g), mp 162°–162.5° C., as a yellow crystalline solid.

EXAMPLE 5

Compounds 2 to 5

Acetone cyanohydrin (0.5 ml) was added to a stirred solution of 5,6-dihydro-4-(2-nitrobenzoyloxy)-6-phenyl-pyridine-2(1H)-one (7.5 g) and triethylamine (6.7 g) in dry dichloromethane (100 ml) and the solution was stirred at ambient temperature for 18 hours. The solution was washed successively with 2N hydrochloric acid (25 ml) and water (3×25 ml) and extracted with 5% w/v aqueous sodium carbonate solution (4×50 ml). The combined extracts were acidified with concentrated hydrochloric acid and the acidic solution extracted with dichloromethane (3×75 ml). The combined extracts were washed with water (3×50 ml), dried over magnesium sulphate and evaporated under reduced pressure to give a brown solid which was recrystallised from a mixture of toluene and hexane (7:1; 40 ml) to give 3-(2-nitrobenzoyl)-6-phenylpiperidine-2,4-dione (4.7 g), mp 146°–150° C., as a salmon coloured crystalline solid.

By proceeding in a similar manner but replacing 5,6-dihydro-4-(2-nitrobenzoyloxy)-6-phenylpyridin-2(1H)-one with 5,6-dihydro-4-(4-chloro-2-nitrobenzoyloxy)-6-phenylpyridine-2(1H)-one there was prepared:

3-(4-chloro-2-nitrobenzoyl)-6-phenylpiperidine-2,4-dione, mp 91°–94° C. [recrystallised from a mixture of carbon tetrachloride and hexane (20:1; 42 ml)] as a light brown crystalline solid.

By proceeding in a similar manner but replacing 5,6-dihydro-4-(2-nitrobenzoyloxy)-6-phenylpyridin-2(1H)-one with 5,6-dihydro-4-(2-nitrobenzoyloxy)-1-methyl-6-phenylpyridin-2-(1H)-one there was prepared:

1-methyl-3-(2-nitrobenzoyl)-6-phenylpiperidine-2,4-dione, mp 144°–146° C. [recrystallised from a mixture of toluene and hexane (4:1; 10 ml)] as a buff crystalline solid.

By proceeding in a similar manner but replacing 5,6-dihydro-4-(2-nitrobenzoyloxy)-6-phenylpyridine-2(1H)-one with 5,6-dihydro-6,6-dimethyl-4-(2-nitrobenzoyloxy)pyridin-2-(1H)-one there was prepared:

6,6-dimethyl-3-(2-nitrobenzoyl)piperidine-2,4-dione, mp 190°–191° C. [recrystallised from a mixture of toluene and hexane (1:1; 25 ml)] as a cream crystalline solid.

REFERENCE EXAMPLE 1

Triethylamine (3.4 ml) was added at 0°–5° C. to a stirred solution of 2-nitrobenzoyl chloride (4.9 g) and 6-phenylpiperidine-2,4-dione (5 g) in dry dichloromethane (100 ml) and the mixture stirred at ambient temperature for 3.5 hours. The solution was washed successively with 2N hydrochloric acid (25 ml), water (2×25 ml), 5% w/v aqueous sodium carbonate solution (25 ml) and water (3×25), dried over magnesium sulphate and evaporated under reduced pressure to give a pale yellow solid which was recrystallised from a mixture of ethyl acetate and hexane (4:1; 20 ml) to give 5,6-dihydro-4-(2-nitrobenzoyl)-6-phenylpyridin-2(1H)-one (4.8 g), mp 139°–141° C., as a light yellow crystalline solid.

By proceeding in a similar manner but replacing 2-nitrobenzoyl chloride with 4-chloro-2-nitrobenzoyl chloride there was prepared:

5,6-dihydro-4-(4-chloro-2-nitrobenzoyloxy)-6-phenylpyridin-2(1H)-one, mp 116°–118° C. [recrystallised from a mixture of carbon tetrachloride and hexane (8:1; 5 ml)] as a pale yellow crystalline solid.

By proceeding in a similar manner but replacing 6-phenylpiperidine-2,4-dione with 1-methyl-6-phenylpiperidine-2,4-dione there was prepared:

5,6-dihydro-4-(2-nitrobenzoyloxy)-1-methyl-6-phenylpyridin-2(1H)-one, as a dark brown gum.

By proceeding in a similar manner but replacing 6-phenylpiperidine-2,4-dione with 6,6-dimethylpiperidine-2,4-dione there was prepared:

5,6-dihydro-6,6-dimethyl-4-(2-nitrobenzoyloxy)pyridin-2(1H)-one, mp 141°–142.5° C. [recrystallised from a mixture of toluene and hexane (5:1; 30 ml)], as a light brown crystalline solid.

EXAMPLE 6

Compounds 6 to 10

A solution of 4-chloro-2-nitrobenzoyl chloride (5.8 g) in dry dichloromethane (10 ml) was added over 5 minutes to a stirred solution of piperidine-2,4-dione (3.0 g) and triethylamine (5.5 ml) in dry dichloromethane (100 ml) and the mixture was stirred at ambient temperature for 3 hours. Acetone cyanohydrin (0.5 ml) was added and the mixture was stirred at ambient temperature for 18 hours. The solution was washed successively with 2N hydrochloric acid (50 ml) and water (2×100 ml), dried over sodium sulphate and evaporated under reduced pressure to give a solid residue which was recrystallised from ethyl acetate (70 ml) to give 3-(4-chloro-2-nitrobenzoyl)piperidine-2,4-dione (1.6 g), mp 161°–164° C., as a light brown crystalline solid.

Piperidine-2,4-dione is a known compound [S. Toda et al, J. Antibiotics XXXIII, 173 (1980)].

By proceeding in a similar manner but replacing piperidine-2,4-dione with 5-methylpiperidine-2,4-dione there was prepared 3-(4-chloro-2-nitrobenzoyl)-5-methylpiperidine-2,4-dione, mp 156°–158° C. [recrystallised from toluene], as a yellow crystalline solid.

By proceeding in a similar manner but replacing piperidine-2,4-dione with 1-methylpiperidine-2,4-dione there was prepared 3-(4-chloro-2-nitrobenzoyl)-1-methylpiperidine-2,4-dione, m.p. 143°–144° C. [recrystallised from a mixture of ethyl acetate and hexane], as a reddish-brown crystalline solid.

By proceeding in a similar manner but replacing piperidine-2,4-dione with 6-methyl-6-phenylpiperidine-2,4-dione there was prepared 3-(4-chloro-2-nitrobenzoyl)-6-methyl-6-phenylpiperidine-2,4-dione, mp 158°–159° C. [recrystallised from a mixture of toluene and hexane (1:1)], as a cream crystalline solid.

By proceeding in a similar manner but replacing piperidine-2,4-dione with 6-methylpiperidine-2,4-dione there was prepared 3-(4-chloro-2-nitrobenzoyl)-6-methylpiperidine-2,4-dione, mp 170°–172° C. [recrystallised from a mixture of ethyl acetate and hexane (1:1)], as a yellow crystalline solid.

EXAMPLE 7

Compounds 11 to 18, 20 to 49, 52 to 65, 68 to 86, 88 to 103 and 110 to 147

By proceeding in a similar manner to that hereinbefore described in Example 6 there were prepared the compounds of general formula I defined in Tables I and II which follow. In Table I, $R^2$ represents a group $(R^8)_n$-phenyl-.

TABLE I

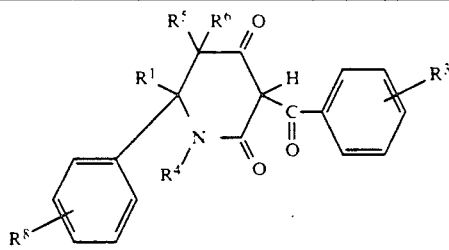

| Compound No. | $R^1$ | $R^3$ | $R^4$ | $R^5$ | $R^6$ | $R^8$ | mp °C. |
|---|---|---|---|---|---|---|---|
| 11 | H | 3,4-Cl$_2$ | H | H | H | H | 166–167 |
| 12 | H | 3-Br | H | H | H | H | 126–127 |
| 13 | H | 2,6-Cl$_2$ | H | H | H | H | 180.5–181.5 |
| 14 | H | 2-NO$_2$-5-CH$_3$ | H | H | H | H | 161–163 |
| 15 | H | 4-CF$_3$ | H | H | H | H | 197–199 |
| 16 | H | 4-F | H | H | H | H | 172–173 |
| 17 | H | 2-Cl | H | H | H | H | 139–142 |
| 18 | H | 2-CF$_3$ | H | H | H | H | 149.5–151 |
| 20 | H | 2,4-bisCF$_3$ | H | H | H | H | 78–80 |
| 21 | H | 2-Br | H | H | H | H | 143–145 |
| 22 | H | 2-I | H | H | H | H | 158–160 |
| 23 | H | 2-CH$_3$ | H | H | H | H | 151–152 |
| 24 | H | H | H | H | H | H | 198–200 |
| 25 | H | 2-Cl-4-F | H | H | H | H | 130–131 |
| 26 | H | 2-NO$_2$-4-Br | H | H | H | H | Oil |
| 27 | H | 2-NO$_2$-4-CF$_3$ | H | H | H | H | 130–131 |
| 28 | H | 2-OCH$_3$ | H | H | H | H | Oil |
| 29 | H | 2-NO$_2$-4-CH$_3$CO | H | H | H | H | 178–179 |
| 30 | H | 2-SCH$_3$ | H | H | H | H | Oil |
| 31 | H | 2-OCF$_3$ | H | H | H | H | 114–115 |
| 32 | H | 2,3,4-Cl$_3$ | H | H | H | H | 97–98 |
| 33 | H | 2,4,5-Cl$_3$ | H | H | H | H | Oil |
| 34 | H | 2-NO$_2$-4-OCH$_3$ | H | H | H | H | 152–153 |
| 35 | H | 2-NO$_2$-5-Cl | H | H | H | H | 168–169 |
| 36 | H | 2-OC$_2$H$_5$ | H | H | H | H | 66–67.5 |
| 37 | H | 3-NO$_2$ | H | H | H | H | 140–141.5 |
| 38 | H | 3-Cl | H | H | H | H | 141.5–143 |
| 39 | H | 3-OCF$_3$ | H | H | H | H | 130–131 |
| 40 | H | 3-CF$_3$ | H | H | H | H | 138.5–140 |
| 41 | H | 3-CH$_3$ | H | H | H | H | 146.5–147.5 |
| 42 | H | 3-OCH$_3$ | H | H | H | H | 132–134 |
| 43 | H | 4-tertC$_4$H$_9$ | H | H | H | H | 170.5–172.5 |
| 44 | H | 4-I | H | H | H | H | 212–214 |
| 45 | H | 2-NO$_2$-4-Cl | H | H | H | 3,4-F$_2$ | 86–89 |
| 46 | H | 2-NO$_2$-4-Cl | H | H | H | 4-CH$_3$ | 66–69 |
| 47 | H | 2-NO$_2$-4-Cl | H | H | H | 4-OCH$_3$ | 73–74 |

TABLE I-continued

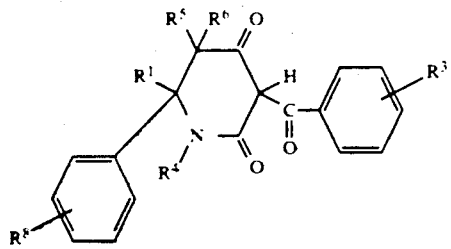

| Compound No | R¹ | R³ | R⁴ | R⁵ | R⁶ | R⁸ | mp °C |
|---|---|---|---|---|---|---|---|
| 48 | H | 2-NO₂-4-Cl | H | H | H | 3-Cl | 130.5-132.5 |
| 49 | H | 2-NO₂-4-Cl | H | H | H | 4-SCH₃ | 93-96 |
| 52 | H | 2-NO₂-4-Cl | H | H | H | 2-Br | 109-112 |
| 53 | H | 2-NO₂-4-Cl | CH₃ | H | H | 2-OCH₃ | 151-153 |
| 54 | H | 2-NO₂-4-Cl | CH₃ | H | H | 4-OC₂H₅ | 119-121 |
| 55 | H | 2-NO₂-4-Cl | CH₃ | H | H | 4-SCH₃ | 75-77 |
| 56 | H | 2-NO₂-4-Cl | CH₃ | H | H | H | 60-62 |
| 112 | H | 2-CF₃-4-F | H | H | H | H | 154-156 |
| 113 | H | 2-Cl-4-CF₃ | H | H | H | H | 126-128 |

TABLE II

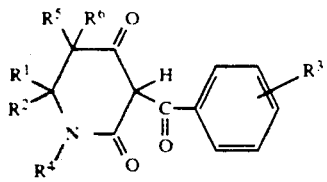

| Compound No | R¹ | R² | R³ | R⁴ | R⁵ | R⁶ | mp °C |
|---|---|---|---|---|---|---|---|
| 57 | H | H | 2,4-diNO₂ | H | H | H | 151-154 |
| 58 | H | H | 2-NO₂-5-Cl | H | H | H | 165.5-167.5 |
| 59 | H | H | 2-NO₂ | H | H | H | 206-208 |
| 60 | H | H | 2-Cl | H | H | H | 209-210 |
| 61 | H | H | 3-CF₃ | H | H | H | 198-201 |
| 62 | H | H | 2,4-Cl₂ | H | H | H | 142-144 |
| 63 | H | H | 2-NO₂-5-CH₃ | H | H | H | 163-165 |
| 64 | H | H | 2,4-bisCF₃ | H | H | H | 162-165 |
| 65 | H | H | 2-CF₃ | H | H | H | 189-191 |
| 68 | H | H | 2,5-Cl₂ | H | H | H | 164-166 |
| 69 | H | H | 2-OC₂H₅ | H | H | H | 101-104 |
| 70 | H | H | 2,3,4-Cl₃ | H | H | H | 172-176 |
| 71 | H | H | 2,4,5-Cl₃ | H | H | H | 139.5-140.5 |
| 72 | H | H | 2-NO₂-4-Br | H | H | H | 168-171 |
| 73 | H | H | 2-NO₂-4-CN | H | H | H | >250° C. |
| 74 | H | H | 2-NO₂-4-CF₃ | H | H | H | 154-156 |
| 75 | H | H | 2-NO₂-4-F | H | H | H | 170-172 |
| 76 | H | H | 2-CH₃-3-NO₂ | H | H | H | 161-163 |
| 77 | H | H | 2-CH₃-5-NO₂ | H | H | H | 198-200 |
| 78 | H | H | 2-Br | H | H | H | 163-165 |
| 79 | H | H | 2-OCH₃ | H | H | H | 149-153 |
| 80 | H | H | 3-NO₂ | H | H | H | 232-234 |
| 81 | H | H | 3-Br | H | H | H | 202-204 |
| 82 | H | H | 3-OCF₃ | H | H | H | 151-152 |
| 83 | H | H | 3-OCH₃ | H | H | H | 139-142 |
| 84 | H | H | 3-Cl | H | H | H | 190-193 |
| 85 | H | H | 3-CH₃ | H | H | H | 157-160 |
| 86 | H | H | 4-NO₂ | H | H | H | 212-214 |
| 88 | H | H | 4-Cl | H | H | H | 182-184 |
| 89 | H | H | 4-CN | H | H | H | 239-243 |
| 90 | H | H | 4-Br | H | H | H | 179-182 |
| 91 | H | H | 4-CH₃ | H | H | H | 176-179 |
| 92 | H | H | 4-OCH₃ | H | H | H | 138-140 |
| 93 | H | CH₃ | 2-NO₂-4-Cl | H | CH₃ | H | 146-148 |
| 94 | —(CH₂)₅— | | 2-NO₂-4-Cl | H | H | H | 150-152 |
| 95 | H | H | 2-NO₂-4-Cl | H | CH₃ | CH₃ | 147-149 |
| 96 | H | H | 2-NO₂-4-Cl | CH₃ | CH₃ | CH₃ | 124-126 |
| 97 | CH₃ | CH₃ | 2,4-bisCF₃ | H | H | H | 175-175.5 |
| 98 | CH₃ | CH₃ | 2-NO₂-4-F | H | H | H | 135-136 |
| 99 | CH₃ | CH₃ | 2-NO₂-4-CF₃ | H | H | H | 147-150 |
| 100 | CH₃ | CH₃ | 2,3,4-Cl₃ | H | H | H | 273-275 |
| 101 | CH₃ | CH₃ | 2,4,5-Cl₃ | H | H | H | 176-178 |
| 102 | CH₃ | CH₃ | 2-NO₂-4-Br | H | H | H | 144-147 |
| 103 | CH₃ | CH₃ | 2-NO₂-4-SO₂CH₃ | H | H | H | 168-170 |

TABLE II-continued

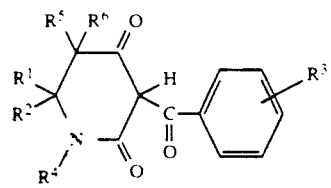

| Compound No | R¹ | R² | R³ | R⁴ | R⁵ | R⁶ | mp °C. |
|---|---|---|---|---|---|---|---|
| 110 | H | H | 2-NO₂-4-SO₂CH₃ | H | H | H | 157-158 |
| 111 | CH₃ | CH₃ | 2-NO₂-4-OCH₃ | H | H | H | 164-166 |
| 114 | H | H | 2-NO₂-4-CO₂Et | H | H | H | 135-137 |
| 115 | H | H | 2-Cl-4-CF₃ | H | H | H | 108-110 |
| 116 | H | H | 2-CF₃-4-F | H | H | H | 179-181 |
| 117 | CH₃ | H | 2-NO₂-4-CF₃ | H | H | H | 126-128 |
| 118 | H | H | 2-NO₂-4-CF₃ | CH₃ | CH₃ | CH₃ | 133-134 |
| 119 | H | H | 2-NO₂-4-OCH₃ | H | H | H | 173-175 |
| 120 | CH₃ | CH₃ | 2-NO₂-4-CO₂Et | H | H | H | 184-185 |
| 121 | CH₃ | CH₃ | 2-NO₂-4-CH₃ | H | H | H | 165-167 |
| 122 | H | H | 4-tertC₄H₉ | H | H | H | 159-161 |
| 123 | H | H | 2-NO₂-4,5-Cl₂ | H | H | H | 146-148 |
| 124 | H | H | 2-NO₂-4-CH₃CO | H | H | H | 139-141 |
| 125 | H | H | 2-NO₂-4-CH₃ | H | H | H | 168-170 |
| 126 | H | H | 2-Cl-4-SO₂CH₃ | H | H | H | 187-188 |
| 127 | H | H | 2-NO₂-4-Cl-5-CH₃ | H | H | H | 163-165 |
| 128 | H | H | 2-Cl-5-NO₂ | H | H | H | 131-133 |
| 129 | H | H | 2-CH₃-4-Br | H | H | H | 156-158 |
| 130 | H | H | 3-Br-4-CH₃ | H | H | H | 168-170 |
| 131 | H | H | 2-SCH₃ | H | H | H | 116-118 |
| 132 | H | H | 2-CH₃ | H | H | H | 217-219 |
| 133 | H | H | 4-I | H | H | H | 144-146 |
| 134 | H | H | 3,5-(CF₃)₂ | H | H | H | 137-139 |
| 135 | CH₃ | CH₃ | 2-Cl-4-SO₂CH₃ | H | H | H | 216 |
| 136 | CH₃ | CH₃ | 2-CF₃-4-F | H | H | H | 159-161 |
| 137 | CH₃ | CH₃ | 2-NO₂-4,5-Cl₂ | H | H | H | 179-180 |
| 138 | CH₃ | CH₃ | 2-NO₂-4-Cl-5-CH₃ | H | H | H | 188-189 |
| 139 | CH₃ | CH₃ | 2-NO₂-4-CN | H | H | H | 169-170.5 |
| 140 | H | H | 2-NO₂-4-SO₂CH₃ | CH₃ | CH₃ | CH₃ | 164-166 |
| 141 | H | H | 2-NO₂-4-CF₃ | H | CH₃ | H | 132-134 |
| 142 | H | H | 2-NO₂-4-CF₃ | H | CH₃ | CH₃ | 145-146 |
| 143 | —(CH₂)₅— | | 2-NO₂-4-CF₃ | H | H | H | 151-153 |
| 144 | CH₃ | C₂H₅ | 2-NO₂-4-CF₃ | H | H | H | 163-164 |
| 145 | C₂H₅ | C₂H₅ | 2-NO₂-4-CF₃ | H | H | H | 182-184 |
| 146 | CH₃ | CH₃ | 2-NO₂-4-CF₃ | CH₃ | H | H | 124-125 |
| 147 | CH₃ | CH₃ | 3,5-(CF₃)₂ | H | H | H | 166-167 |

EXAMPLE 8

Compounds 104 and 105

A solution of 4-chloro-2-nitrobenzoyl chloride (4.4 g) in dry dichloromethane (5 ml) was added at 5°-10° C. to a stirred solution of 5-phenylcyclohexane-1,3-dione [3.7 g] and triethylamine (2.8 ml) in dry dichloromethane (50 ml), and the mixture was stirred at ambient temperature for 18 hours. Triethylamine (8.4 ml) and acetone cyanohydrin (0.4 ml) were added successively to the solution and the mixture was stirred at ambient temperature for 4 hours. The resulting solution was washed successively with 2N hydrochloric acid (25 ml) and water (3×25 ml), dried over sodium sulphate and evaporated under reduced pressure to give a brown solid which was recrystallised from acetonitrile to give 2-(4-chloro-2-nitrobenzoyl)-5-phenylcyclohexane-1,3-dione (4.2 g), mp 144°-145° C., as a light cream crystalline solid.

By proceeding in a similar manner but replacing 5-phenylcyclohexane-1,3-dione with 4-carbethoxy-5-phenylcyclohexane-1,3-dione there was prepared: 4-carbethoxy-2-(4-chloro-2-nitrobenzoyl)-5-phenylcyclohexane-1,3-dione, mp 57°-59° C. [purified by column chromatography] as a yellow crystalline solid.

EXAMPLE 9

Compounds 106 and 107

2-Nitro-4-trifluoromethylbenzoyl chloride (4 g) was added at 0°-5° C. to a stirred solution of triethylamine (2.2 ml) and 6-methyltetrahydropyran-2,4-dione (2 g) in dry acetonitrile (25 ml) and the mixture was stirred at ambient temperature for 4 hours. Triethylamine (6.4 ml) and acetone cyanohydrin (0.3 ml) were added successively to the solution and the mixture stirred at ambient temperature for a further 2 hours. The mixture was diluted with dichloromethane (50 ml) and washed successively with 2N hydrochloric acid (20 ml) and water (3×20 ml). The dichloromethane solution was dried over sodium sulphate and evaporated under reduced pressure to give a brown gum which was triturated with a mixture of chloroform and hexane (1:1, 20 ml) to give 3-(2-nitro-4-trifluoromethylbenzoyl)-6-methyltetrahydropyran-2,4-dione (2.2 g), mp 135°-136.5° C., as a light cream crystalline solid.

By proceeding in a similar manner but using 6-phenyltetrahydropyran-2,4-dione instead of 6-methyltetrahydropyran-2,4-dione there was prepared 3-(2-nitro-4-trifluoromethylbenzoyl)-6-phenyltetrahydropyran-2,4-dione, mp. 160°-161° C.

EXAMPLE 10

Compound 108

A solution of 4-chloro-2-nitrobenzoyl chloride (1 g) in dry dichloromethane (5 ml) was added at 0°-10° C. to a stirred solution of triethylamine (0.62 ml) and 5-(2-ethylthiopropyl)-6-carbethoxycyclohexane-1,3-dione (1.3 g) in dry dichloromethane (20 ml) and the mixture stirred at ambient temperature for 2 hours. Triethylamine (1.9 g) and acetone cyanohydrin (0.1 ml) were added successively to the solution and the mixture stirred at ambient temperature for a further 18 hours. The mixture was washed successively with 2N hydrochloric acid (10 ml) and water (2×10 ml) dried over magnesium sulphate and evaporated under reduced pressure to give 2-(4-chloro-2-nitrobenzoyl)-5-(2-ethylthiopropyl)-6-carbethoxycyclohexane-1,3-dione (0.6 g), mp 102°-104° C., as an orange crystalline solid.

EXAMPLE 11

Compound 109

A solution of 2-nitro-4-trifluoromethylbenzoyl chloride (2.6 g) in dry acetonitrile (8 ml) was added at ambient temperature to a stirred solution of 6-methyl-6-trifluoromethylpiperidine-2,4-dione (2 g) and dry triethylamine (1.4 ml) in dry acetonitrile (25 ml) and the mixture stirred at ambient temperature for 18 hours.

Dry triethylamine (4.5 ml) and acetone cyanohydrin (0.5 ml) were added consecutively and the mixture stirred at ambient temperature for 8 hours. The reaction mixture was washed successively with 2N hydrochloric acid (25 ml) and water (3×50 ml), dried over magnesium sulphate and evaporated under reduced pressure to give a yellow gum which was recrystallised from a mixture of toluene and hexane (15 ml:10 ml) to give 3-(2-nitro-4-trifluoromethylbenzoyl)-6-methyl-6-trifluoromethylpiperidine-2,4-dione (3.2 g) mp 164.5°-165.5° C., as a yellow crystalline solid.

EXAMPLE 12

Compound 66

Dry triethylamine (1.33 g) was added at 0°-5° C. to a stirred suspension of piperidine-2,4-dione (1.13 g), anhydrous zinc chloride (1.64 g) and benzoyl cyanide (1.31 g) in dry dichloromethane (50 ml) and the mixture stirred at ambient temperature for 18 hours. The mixture was washed successively with 2N hydrochloric acid (2×30 ml) and water (3×30 ml) dried over magnesium sulphate and evaporated under reduced pressure to give a pale yellow solid which was recrystallised from acetonitrile (0.5 ml) to give 3-benzoylpiperidine-2,4-dione (0.5 g), mp 164°-165° C., as a cream crystalline solid.

EXAMPLE 13

Compound 87

Dry triethylamine (3.24 g) was added at 0°-5° C. to a stirred solution of diethyl cyanophosphate (1.96 g), 4-trifluoromethylbenzoic acid (2.28 g) and piperidine-2,4-dione (1.13 g) in dry dimethylformamide (50 ml) and the mixture stirred at ambient temperature for 5 hours. The mixture was diluted with dichloromethane (70 ml) and the solution washed successively with 2N hydrochloric acid (70 ml) and water (5×30 ml). The dichloromethane solution was dried over magnesium sulphate and evaporated under reduced pressure to give a brown solid which was recrystallised from toluene (11 ml) to give 3-(4-trifluoromethylbenzoyl)piperidine-2,4-dione (0.44 g), mp 197°-200° C., as a pale green crystalline solid.

EXAMPLE 14

Compound 67

A solution of 3,4-dichlorobenzoyl chloride (2.1 g) in dry acetonitrile (10 ml) was added at ambient temperature to a stirred solution of piperidine-2,4-dione (1.13 g) and dry triethylamine (1.31 g) in dry acetonitrile (50 ml) and the mixture stirred at ambient temperature for 18 hours. Potassium cyanide (0.06 g) dry triethylamine (3.1 g) and tris-(3,6-dioxaheptyl)amine (0.5 ml) were added successively and the mixture stirred at ambient temperature for 24 hours. The mixture was evaporated under reduced pressure and the residue dissolved in dichloromethane (50 ml). The dichloromethane solution was washed successively with 2N hydrochloric acid (2×30 ml) and water (3×30 ml), dried over magnesium sulphate and evaporated under reduced pressure to give a brown solid which was purified by column chromatography to give 3-(3,4-dichlorobenzoyl)piperidine-2,4-dione (0.37 g) mp 171.5°-174.5° C., as a cream crystalline solid.

EXAMPLE 15

Compound 19

A suspension of 5,6-dihydro-4-(2-fluorobenzoyloxy)-6-phenylpyridin-2(1H)-one (10.9 g) in dichloroethane (10 ml) was added at −5° to +5° C. to a stirred mixture of aluminium chloride (9.3 g) and dichloroethane (50 ml) and the mixture stirred at ambient temperature for 4 hours. The reaction mixture was added to a mixture of ice and concentrated hydrochloric acid (400 g/75 ml) and the acidic mixture extracted with dichloromethane (3×200 ml). The combined extracts were washed with water (2×200 ml), dried over magnesium sulphate and evaporated under reduced pressure to give a yellow oil which was recrystallised from a mixture of methanol and water (25 ml+5 ml) to give 3-(2-fluorobenzoyl)-6-phenylpiperidine-2,4-dione, (2.1 g) mp 115°-116.5° C., as a pale yellow crystalline solid.

By proceeding in a similar manner to that described in Reference Example 1 but replacing 2-nitrobenzoyl chloride with 2-fluorobenzoyl chloride there was prepared: 5,6-dihydro-4-(2-fluorobenzoyloxy)-6-phenylpyridin-2(1H)-one, mp 148°-149° C. [recrystallised from methanol] as a colourless, crystalline solid.

EXAMPLE 16

Compounds 50 and 51

A solution of m-chloroperbenzoic acid (1.48 g) in dry dichloromethane (40 ml) was added to a stirred solution of 3-(4-chloro-2-nitrobenzoyl)-6-(4-methylthiophenyl)-piperidine-2,4-dione (1.5 g) in dry dichloromethane (60 ml) at 5°-10° C. and the mixture stirred at ambient temperature for 18 hours. The mixture was washed successively with 2N sodium metabisulphite solution (25 ml) and water (2×50 ml), dried over magnesium sulphate and evaporated under reduced pressure to give a cream solid which was recrystallised from a mixture of dioxan and hexane (25:16 ml) to give 3-(4-chloro-2-nitrobenzoyl)-6-(4-methylsulphonylphenyl)piperidine-2,4-dione (0.57 g), mp 296°-9° C., as a pale yellow crystalline solid.

By proceeding in a similar manner but using half the quantity of m-chloroperbenzoic acid there was prepared 3-(4-chloro-2-nitrobenzoyl)-6-(4-methylsulphinylphenyl)-piperidine-2,4-dione. mp 248°-251° C.

EXAMPLE 17

A mixture of methyl 6,6-dimethylpiperidine-2,4-dione-3-carboxylate (26.3 g), water (30 ml) and concentrated hydrochloric acid (3 drops) in acetonitrile (300 ml) was heated at reflux for 4 hours. The cooled solution was evaporated under reduced pressure and the residue recrystallised from water (50 ml) to give 6,6-dimethylpiperidine-2,4-dione (7.3 g), mp 183°-184° C., as a cream crystalline solid.

By proceeding in a similar manner there were prepared the piperidine diones listed in Tables III and IV.

TABLE III

| $R^1$ | $R^4$ | $R^5$ | $R^6$ | $R^8$ | mp °C |
|---|---|---|---|---|---|
| H | H | H | H | H | 171-172 |
| CH$_3$ | H | H | H | H | 185-187 |
| H | CH$_3$ | H | H | H | 109-111 |
| H | H | H | H | 3,4-F$_2$ | 116-120 |
| H | H | H | H | 4-CH$_3$ | 153-155 |
| H | H | H | H | 4-OCH$_3$ | 171-172 |
| H | H | H | H | 3-Cl | 105-107 |
| H | H | H | H | 4-SCH$_3$ | 169-173 |
| H | H | H | H | 2-Br | 93-95 |
| H | CH$_3$ | H | H | 2-OCH$_3$ | 168-170 |
| H | CH$_3$ | H | H | 4-OC$_2$H$_5$ | 130-133 |
| H | CH$_3$ | H | H | 4-SCH$_3$ | 99-102 |

TABLE IV

| $R^1$ | $R^2$ | $R^4$ | $R^5$ | $R^6$ | mp °C |
|---|---|---|---|---|---|
| CH$_3$ | CH$_3$ | H | H | H | 182-183 |
| H | H | H | H | H | 100-101 |
| H | H | H | CH$_3$ | H | 86-89 |
| H | CH$_3$ | H | H | H | 120-123 |
| H | CH$_3$ | H | CH$_3$ | H | 115-118 |
| —(CH$_2$)$_5$— | | H | H | H | 153-155 |
| H | H | H | CH$_3$ | CH$_3$ | 125-127 |
| CF$_3$ | CH$_3$ | H | H | H | 153-154 |
| CH$_3$ | C$_2$H$_5$ | H | H | H | 136-137 |
| C$_2$H$_5$ | C$_2$H$_5$ | H | H | H | 129-130 |
| H | H | CH$_3$ | H | H | Oil |
| H | H | CH$_3$ | CH$_3$ | CH$_3$ | 52-54 |
| CH$_3$ | CH$_3$ | CH$_3$ | H | H | 101-102 |

REFERENCE EXAMPLE 2

A solution of methyl 3-(ethoxycarbonylacetamido)-3-methylbutyrate (45 g) and sodium metal (4.22 g) in anhydrous methanol (450 ml) was heated at a reflux for 3 hours. The cooled mixture was evaporated under reduced pressure and the residue dissolved in water (200 ml). The aqueous solution was washed with ether (3×100 ml), acidified with 2N hydrochloric acid and the acidic mixture extracted with dichloromethane (3×100 ml). The combined extracts were washed with water (2×100 ml), dried over magnesium sulphate and evaporated under reduced pressure to give methyl 6,6-dimethylpiperidine-2,4-dione-3-carboxylate (26.3 g), mp 170°-172° C., as a cream crystalline solid.

By proceeding in a similar manner but replacing methyl 3-(ethoxycarbonylacetamido)-3-methylbutyrate with ethyl-3-methoxycarbonylacetamido)-3-phenylbutyrate there was prepared: methyl 6-methyl-6-phenyl-piperidine-2,4-dione-3-carboxylate, as a clear red oil.

By proceeding in a similar manner but replacing methyl 3-(ethoxycarbonylacetamido)-3-methylbutyrate with methyl-3-(ethoxycarbonylacetamido)-N-methyl-3-phenylpropionate there was prepared: methyl 1-methyl-6-phenylpiperidine-2,4-dione-3-carboxylate, as a clear orange oil.

By proceeding in a similar manner but replacing methyl 3-(ethoxycarbonylacetamido)-3-methylbutyrate with methyl-3-(ethoxycarbonylacetamido)-3-trifluoromethylbutyrate there was prepared: methyl 6-methyl-6-trifluoromethylpiperidine-2,4-dione-3-carboxylate, mp 150°-152° C., as a cream crystalline solid.

REFERENCE EXAMPLE 3

A solution of ethyl malonoyl chloride (31 g) in dry dichloromethane (50 ml) was added at 0°-5° C. to a well stirred mixture of methyl 3-aminoisovalerate hydrochloride (33.5 g) and dry triethylamine (58.5 ml) in dry dichloromethane (300 ml) and the mixture stirred at ambient temperature for 18 hours. The mixture was washed successively with 2N hydrochloric acid (50 ml), water (50 ml), 2N sodium carbonate (25 ml) and water (3×50 ml) dried over magnesium sulphate and evaporated under reduced pressure to give methyl 3-(ethoxycarbonylacetamido)-3-methylbutyrate (45 g), as a clear orange oil.

By proceeding in a similar manner but replacing methyl 3-aminoisovalerate hydrochloride with methyl-3-methylamino-3-phenylpropionate there was prepared: methyl-3-(ethoxycarbonylacetamido)-N-methyl-3-phenylpropionate, as a clear orange oil.

By proceeding in a similar manner but replacing methyl 3-aminoisovalerate hydrochloride with methyl-3-amino-3-methyl-4,4,4-trifluorobutyrate there was prepared: methyl-3-(ethoxycarbonylacetamido)-3-trifluoromethylbutyrate, as a clear orange oil.

REFERENCE EXAMPLE 4

Concentrated sulphuric acid (80 ml) was added at 0°-5° C. to a stirred solution of methyl cyanoacetate (28 ml) and ethyl 3-hydroxy-3-phenylbutyrate (65 g) and the mixture stirred at ambient temperature for 18 hours. The mixture was added to crushed ice (250 g) and the acidic mixture extracted with dichloromethane (3×100 ml). The combined extracts were washed with water (4×250 ml), dried over sodium sulphate and evaporated under reduced pressure to give ethyl 3-(methoxycarbonylacetamido)-3-phenylbutyrate (43.16 g), as a clear brown oil.

REFERENCE EXAMPLE 5

Thionyl chloride (30 ml) was added at 0°-5° C. to a stirred solution of 3-methylamino-3-phenylpropionic acid (39 g) in anhydrous methanol and the mixture stirred at ambient temperature for 5 hours. The solution was evaporated under reduced pressure and the residue treated with 2N sodium carbonate (350 ml). The solution was extracted with dichloromethane (2×100 ml). The combined extracts were washed with water (250 ml) dried over magnesium sulphate and evaporated under reduced pressure to give methyl-3-methylamino-3-phenylpropionate (36.9 g) as a clear orange oil.

By proceeding in a similar manner but replacing 3-methylamino-3-phenylpropionic acid with 3-amino-3-trifluoromethylbutyric acid there was prepared: methyl 3-amino-3-methyl-4,4,4-trifluorobutyrate as a clear colourless oil.

REFERENCE EXAMPLE 6

A solution of N-methyl-3-phenylisoxazolidin-3-one (45 g) in methanol (510 ml) was hydrogenated at 40 psi over 5% palladium on charcoal (0.5 g) for 6 hours. The mixture was filtered and the filtrate evaporated under reduced pressure to give 3-methylamino-3-phenylpropionic acid (39 g). mp 167°–168° C. as a pale orange crystalline solid.

REFERENCE EXAMPLE 7

A solution of 3-trifluoromethylcrotonic acid (10 g) and liquid ammonia (23 ml) in ammonium hydroxide (27 ml sd=0.88) was heated in a closed steel vessel at 148°–152° C. for 16 hours evaporation of the cooled solution gave 3-amino-3-trifluoromethylbutyric acid (10.2 g). as a viscous colourless oil.

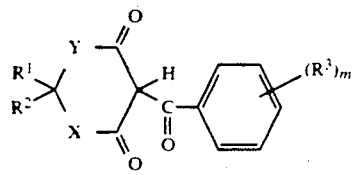 I

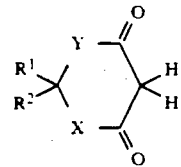 II

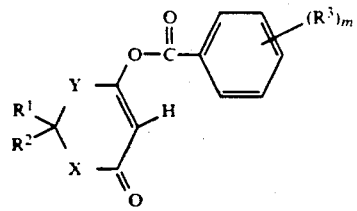 III

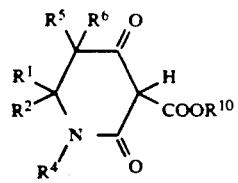 IV $R^1C(R^2)=NR^4$ V

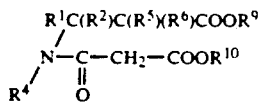 VI

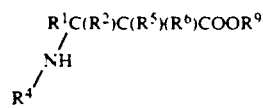 VII $HOOCCH_2-COOR^{10}$ VIII

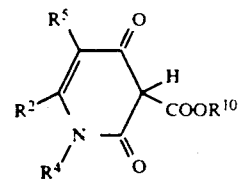 IX

We claim:
1. A 2-benzoylcylic-1,3-dione derivative of the general formula:

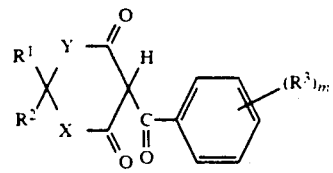 I wherein X is selected from the group consisting of the methylene group, an oxygen atom, a sulphur atom and a group $-NR^4-$. Y represents a methylene group $-C(R^5)(R^6)-$ or the oxygen atom, $R^1$ represents the hydrogen atom or a straight- or branched-chain alkyl group of from 1 to 6 carbon atoms which unsubstituted or substituted by one or more halogen atoms or represents a cycloalkyl group of from 3 to 6 carbon atoms, $R^2$ represents the hydrogen atom or a group $R^7$ or $R^1$ and $R^2$ together represent an alkylene group of from 2 to 6 carbon atoms, $R^3$ represents a halogen atom, a hydroxy, carboxy, nitro or cyano group. an amino or carbamoyl group which is unsubstituted or substituted by one or two straight- or branched-chain alkyl groups of from 1 to 6 carbon atoms, a straight- or branched-chain alkoxycarbonyl or alkanoyl or alkanoylamino group of from 2 to 7 carbon atoms or a group R, RO, RS. RSO or $RSO_2$ in which R represents a straight- or branched-chain alkyl group of from 1 to 6 carbon atoms which is unsubstituted or substituted by one or more halogen atoms, $R^4$ represents the hydrogen atom or a straight- or branched-chain alkyl or alkoxycarbonyl group of from 1 to 6 or from 2 to 7 carbon atoms respectively, $R^5$ represents the hydrogen atom or a straight- or branched-chain alkyl or alkoxycarbonyl group of from 1 to 6 or 2 to 7 carbon atoms respectively, $R^6$ represents the hydrogen atom or a straight- or branched-chain alkyl group of from 1 to 6 carbon atoms, $R^7$ represents a straight- or branched-chain alkyl group of 1 to 6 carbon atoms which is unsubstituted or substituted by one or more halogen atoms or a straight- or branched-chain alkylthio group of from 1 to 6 carbon atoms or by a group $(R^8)_n$-phenyl-S-, or represents a cycloalkyl group of from 3 to 6 carbon atoms, or the tetrahydrothiapyran-3-yl group or represents a group $(R^8)_n$-phenyl- in which $R^8$ represents a halogen atom, a hydroxy, carboxy, nitro or cyano group, an amino or carbamoyl group which is unsubstituted or substituted by one or two straight- or branched-chain alkyl groups of from 1 to 6 carbon atoms, a straight- or branched-chain alkoxycarbonyl or alkanoyl or alkanoylamino group of from 2 to 7 carbon atoms or a group R, RO, RS, RSO or $RSO_2$ in which R represents a straight- or branched-chain alkyl group of from 1 to 6 carbon atoms which is unsubstituted or substituted by one or more halogen atoms, m is zero or an integer from 1 to 5 and n is zero or an integer from 1 to 5, with the proviso that (i) when X represents the methylene group, and Y represents a methylene group $-C(R^5)(R^6)-$ then $R^1$ and $R^2$ do not simultaneously represent a hydrogen atom or a straight- or branched-chain alkyl group of from 1 to 6 carbon atoms, and (ii) if $R^1$ and $R^2$ are hydrogen or $C_1-C_4$ alkyl, Y is $-C(R^5)(R^6)-$ wherein $R^5$ and $R^6$ are hydrogen or $C_1-C_4$ alkyl and X is $-NR^4$ wherein $R^4$ is $C_1-C_4$ alkyl, then m equals 0, 4 or 5, or if m equals 1, 2 or 3 then $R^3$ is hydroxy, carboxy, carbamoyl, or alkoxycarbonyl; or an agriculturally acceptable salt thereof.

2. A compound according to claim 1 wherein $R^1$ represents the hydrogen atom or a straight- or branched-chain alkyl group of from 1 to 6 carbon atoms, $R^2$ represents the hydrogen atom or a group $R^7$, $R^3$ is as defined in claim 1 but does not represent a carbamoyl group, $R^7$ represents a straight- or branched-chain alkyl group of from 1 to 6 carbon atoms which is unsubstituted or substituted by a straight- or branched-chain alkylthio group of from 1 to 6 carbon atoms or by a group $(R^8)_n$-phenyl-S- or represents the cyclohexyl group or the tetrahydrothiapyran-3-yl group or represents a group $(R^8)_n$-phenyl- in which $R^8$ is as defined in claim 1 but does not represents a carbamoyl group, and the other symbols are as defined in claim 1.

3. A compound according to claim 1 wherein Y represents a methylene group $-CR^5R^6-$, X represents a group $-NR^4-$, $R^1$ represents the hydrogen atom or a straight- or branched-chain alkyl group of from 1 to 6 carbon atoms, $R^2$ represents the hydrogen atom or a group $R^7$, $R^3$ is as defined in claim 1 but does not represent a carbamoyl group, $R^7$ represents a straight- or branched-chain alkyl group of from 1 to 6 carbon atoms or represents a group $(R^8)_n$-phenyl- in which $R^8$ is as defined in claim 1 but does not represent a carbamoyl group, and the other symbols are as defined in claim 1.

4. A compound according to claim 1 wherein Y represents a methylene group $-C(R^5)(R^6)-$ wherein $R^5$ and $R^6$ are as defined in claim 1.

5. A compound according to claim 1 wherein X represent a group $-NR^4-$, Y represents a methylene group $-C(R^5)(R^6)-$, $R^2$ represents an alkyl or an unsubstituted or substituted phenyl group as defined in claim 1 for $R^7$ and the other symbols are as defined in claim 1.

6. A compound according to claim 1 wherein $R^2$ represents the hydrogen atom or a straight- or branched-chain alkyl group of from 1 to 6 carbon atoms which is unsubstituted or substituted by one or more halogen atoms or a cycloalkyl group of from 3 to 6 carbon atoms, or represents a group $(R^8)_n$-phenyl-, or $R^1$ and $R^2$ together represent an alkylene group of from 2 to 6 carbon atoms.

7. A compound according to claim 1 wherein $R^1$ represents a straight- or branched-chain alkyl group of from 1 to 6 carbon atoms which is substituted by one or more halogen atoms or a cycloalkyl group of from 3 to 6 carbon atoms and $R^2$ represents a group $(R^8)_n$-phenyl-.

8. A compound according to claim 1 wherein X is selected from the group consisting of the methylene group, an oxygen atom, a sulphur atom and a group $-NR^4-$, in which $R^4$ represents the hydrogen atom or a staight- or branched-chain alkyl group of from 1 to 6 carbon atoms, Y represents a methylene group $-C(R^5)(R^6)-$, $R^1$ represents the hydrogen atom or a straight- or branched-chain alkyl group of from 1 to 6 carbon atoms which is unsubstituted or substituted by one or more halogen atoms or a cycloalkyl group of from 3 to 6 carbon atoms, $R^2$ represents a straight- or branched-chain alkyl group of from 1 to 6 carbon atoms which is substituted by one or more halogen atoms or a cycloalkyl group of from 3 to 6 carbon atoms or $R^1$ and $R^2$ together represent an alkylene group of from 2 to 6 carbon atoms.

9. A compound according to claim 1 wherein X represents the group $-NH-$, Y represents a methylene group $-C(R^5)(R^6)-$, $R^1$ represents the hydrogen atom or a straight- or branched-chain alkyl group of from 1 to 6 carbon atoms, $R^2$ represents the hydrogen atom or a straight- or branched-chain alkyl group of from 1 to 6 carbon atoms.

10. A compound according to claim 1 wherein $(R^3)_m$ substitution is 2-chloro, 2-trifluoromethyl or 2-nitro, with 4-trifluoromethoxy, 4-trifluoromethylthio, 4-trifluoromethylsulphinyl, 4-trifluoromethyl-sulphonyl, 4-chloro, 4-trifluoromethyl or 4-methylsulphonyl.

11. A compound according to claim 10 wherein $(R^3)_m$ substitution comprises 2-nitro substitution.

12. A compound according to claim 10 which lacks a substituent in the 6-position of the benzoyl group.

13. A compound according to claim 1 wherein the compound is one of compound nos. 1-10, 14, 20, 23-27, 34, 45-48, 53-76, 81-83, 94-100, 102-107, 109-111 and 113-121.

14. A herbicidal composition which comprises, as active ingredient, a 2-benzoylcyclic-1,3-dione according to claim 1 or an agriculturally acceptable salt thereof in association with an agriculturally acceptable diluent or carrier and/or surface active agent.

15. A herbicidal composition according to claim 14 which comprises from 0.05 to 90% by weight of active ingredient.

* * * * *